US007947871B2

(12) United States Patent
Shestibratov et al.

(10) Patent No.: US 7,947,871 B2
(45) Date of Patent: May 24, 2011

(54) **METHOD FOR PRODUCING A TRANSGENIC PLANT WITH THE AID OF *AGROBACTERIUM THUMEFACIENS***

(75) Inventors: Konstantin Aleksandrovich Shestibratov, Puschino (RU); Sergey Vladimirovich Dolgov, Puschino (RU)

(73) Assignee: Shemyakin and Ovchinnikov Institute of Bioorganic Chemistry Russian Academy of Sciences, Moscow (RU)

( * ) Notice: Subject to any disclaimer, the term of this patent is extended or adjusted under 35 U.S.C. 154(b) by 256 days.

(21) Appl. No.: 10/531,769

(22) PCT Filed: Oct. 15, 2003

(86) PCT No.: PCT/RU03/00439
§ 371 (c)(1),
(2), (4) Date: Dec. 14, 2005

(87) PCT Pub. No.: WO2004/038023
PCT Pub. Date: May 6, 2004

(65) Prior Publication Data
US 2007/0124835 A1 May 31, 2007

(30) Foreign Application Priority Data

Oct. 24, 2002 (RU) .................. 2002128414

(51) Int. Cl.
*A01H 5/00* (2006.01)
*A01H 1/00* (2006.01)
*C12N 15/09* (2006.01)
*C12N 15/82* (2006.01)
(52) U.S. Cl. ........ 800/279; 800/278; 800/298; 800/294; 800/317.4; 435/430.1; 435/468; 435/430
(58) Field of Classification Search .................. None
See application file for complete search history.

(56) References Cited

U.S. PATENT DOCUMENTS

| | | | |
|---|---|---|---|
| 4,801,545 | A | 1/1989 | Stuart et al. |
| 4,891,316 | A | 1/1990 | Verrips et al. |
| 5,750,870 | A | 5/1998 | Mathews et al. |
| 5,856,154 | A | 1/1999 | Ryals et al. |
| 6,162,965 | A | 12/2000 | Hansen |
| 6,274,791 | B1 | 8/2001 | Dhir et al. |
| 2002/0004944 | A1 | 1/2002 | Baker et al. |

FOREIGN PATENT DOCUMENTS

| | | |
|---|---|---|
| EP | 0 307 841 | 3/1989 |
| RU | 97109836 | 5/1999 |

OTHER PUBLICATIONS

Hansen et al. Trends in Plant Science (1999), vol. 4(6):226-231.*
Partial English Translation of RU 97109836 dated May 10, 1999.
Morozova T. "Genetic Stability of Pure Lines of *Fragaria vesca* L. in Micropropagation and Long-Term Storage in Vitro." *ISHS Acta Horticulturae* 567: IV International Strawberry Symposium, 2002.
Mussinan C., et al. "Organic Acids and Fresh California Strawberries." *J. Agric. Food Chem.* (1975) vol. 23, No. 3, pp. 482-484.
Murashige, T., et al. "A Revised Medium for Rapid Growth and Bio Assays with Tobacco Tissue Cultures." *Physiologia Plantarum* (1962) vol. 15, pp. 472-496.
Olhoft, P.M., et al. "The Role of Thiol Compounds in Increasing Agrobacterium-Mediated Transformation of Soybean Cotyledonary-Node Cells." *Plant Cell Reports* (2001) vol. 20, pp. 731-737.
Perl, A., et al. "Establishment of an Agrobacterium-Mediated Transformation System for Grape (*Vitis vinifera* L.): The Role of Antioxidants during Grape-Agrobacterium Interactions." *Nature Biotechnology* (1996) vol. 14, pp. 624-628.
Roberts., W., et al. "Zeamatin, an Antifungal Protein from Maize with Membrane-Permeabilizing Activity." *Journal of General Microbiology* (1990) vol. 136, pp. 1771-1778.
Rogers., S., et al. "Extraction of Total Cellular DNA from Plants, Algae and Fungi." *Plant Molecular Biology Manual D1* (1994) p. 1-8.
Schestibratov, K., et al. "Plant Regeneration from Excised Cotyledons of *Pinus radiata*." *European Tissue Culture Society* (2001) 43$^{rd}$ International Meeting, PW3-09.
Schestibratov, K., et al. "Molecular Breeding of Strawberry cv Firework for Enhanced Disease Resistance and Taste Improvement by Introduction of thauII and rs-afp3 Genes." *Agricultural Biotechnology International Conference ABIC* (2002).
Stintzi, A., et al. "Plant 'pathogenesis-related' Proteins and Their Role in Defense Against Pathogens." *Biochimie* (1993) vol. 75, pp. 687-706.
Sutter, E., et al. "Direct Regeneration of Strawberry (Fragaria X Ananassa Duch.) from Leaf Disks." *Hort. Biotech. in Vitro Cult. and Breeding* (1997) pp. 243-245.
Szwacka, M., et al. "Variable Properties of Transgenic Cucumber Plants Containing the Thaumatin II Gene from *Thaumatococcus daniellii*." *ACTA Physiologiae Plantarum* (2002) vol. 24, No. 2, pp. 173-185.
Dreipera, D. et al. "Direct Regeneration of Transformed Plants: Transformation of Tobacco Leaf Disks" *Plant Genetic Transformation and Gene Expression. A Laboratory Manual "Mir"* (1991) pp. 119-130.
VINITI Database. Revenkova, E.V. et al. "Development of a New vector System Based on *Agrobacterium tumefaciens* A281 Strain" *Genetic Engineering of Plants* (1994) Abstract.
Nehra, N., et al. "Genetic Transformation of Strawberry by *Agrobacterium tumefaciens* Using a Leaf Disk Regeneration System." *Planet Cell Reports* (1990) vol. 9, pp. 293-298.

(Continued)

*Primary Examiner* — Medina A Ibrahim
(74) *Attorney, Agent, or Firm* — Ladas & Parry LLP

(57) ABSTRACT

The invention relates to an improved method for *agrobacterium* transformation and regeneration of plants. The inventive method is characterized in that it consists in sequentially preparing, inoculating and co-cultivating explants. The preparation of each subsequent lot of plants is carried out after a time interval for transforming plant cells and forming an induced resistance with respect to abiotic and biotic stresses in a leaf discs, thereby making it possible to reduce a necrosis degree and the number of somaclonal variations of the transgenic plants.

15 Claims, 5 Drawing Sheets

OTHER PUBLICATIONS

James, D., et al. "Agrobacterium-Mediated Transformation of the Cultivated Strawberry (Fragaria x Anannassa Duch.) Using Disarmed Binary Vectors." *Plant Science* (1990) vol. 69, pp. 79-94.

Abad, L., et al. "Antifunal Activity of Tobacco Osmotin Has Specificity and Involves Plasma Membrane Permeabilization." *Plant Science* (1996) vol. 118, pp. 11-23.

de Mesa, M., et al. "Agrobacterium Cells as Microprojectile Coating: A Novel Approach to Enhance Stable Transformation Rates in Strawberry." *Aus. J. Plant Physio.* (2000) vol. 27, pp. 1093-1100.

Dolgov, S.V., et al. "Expression of Thaumatin II Gene in Horticultural Crops." *Genetics and Breeding for Crop Quality and Resistance* (1999) pp. 165-172.

du Plessis, H., et al. "Efficient Genetic Transformation of Strawberry (Fragaria x Ananassa Duch.) Cultivar Selekta." *Hort. Biotech. In Vitro Cult. and Breeding* (1997) pp. 289-293.

Edens, L., et al. "Cloning of cDNA Encoding the Sweet-Tasting Plant Protein Thaumatin and its Expression in *Escherichia coli*." *Gene* (1982) vol. 18, p. 1-12.

Humara, J.M., et al. "*Agrobacterium tumefaciens*-Mediated Transformation of *Pinus pinea* L. Cotyledons: An Assessment of Factors Influencing the Efficiency of uidA Gene Transfer." *Plant Cell Reports* (1999) vol. 19, pp. 51-58.

Linthorst, H., et al. "Constitutive Expression of Pathogenesis-Related Proteins PR-1, GRP, and PR-S in Tobacco Has No Effect on Virus Infection." *The Plant Cell* (1989) vol. 1, pp. 285-291.

Maniatis, T., et al. "Molecular Cloning: A Laboratory Manual" *Cold Spring Harbor Laboratory* (1982) pp. 1.19-1.29.

Marcotrigiano M., et al. "Histogenic Instability in Tissue Culture-Proliferated Strawberry Plants." *J. Amer. Soc. Hort. Sci.* (1987) vol. 112, No. 3, pp. 583-587.

Lan Zhou, et al. "Wound-Inducible Genes in Plants" Department of Biochemistry and Biophysics (1999) pp. 127-158.

Martin Heil, et al. "Induced System Resistance (ISR) Against Pathogens in the Context of Induced Plants Defences" Annals of Botany 89: (2002) pp. 503-512.

L.C. Van Loon "Induced Resistance in Plants and the Role of Pathogenesis-related Proteins" European Journal of Plant Pathology 103: (1997) pp. 753-765.

Emma Wanjiru Gachomo, et al. "The Molecular Initiation and Subsequent Acquisition of Disease Resistance in Plants" African Journal of Biotechnology (Feb. 2003) vol. 2(2) pp. 26-32.

* cited by examiner

SEQUENCE LISTING

<160> NUMBER OF SEQ ID NOS: 4

<210> SEQ ID NO 1
<211> LENGTH: 962
<212> TYPE: DNA
<213> ORGANISM: ARTIFICIAL SEQUENCE
<220> FEATURE:
<223> OTHER INFORMATION: DNA fragment containing thaumatin II gene

<400> SEQUENCE: 1

| | | | | | | |
|---|---|---|---|---|---|---|
| tctagactcg | aggaattcta | tggccgccac | cacttgcttc | ttcttcctct | tcccttcct | 60 |
| cctcctcctc | acgctctccc | gcgctgccac | cttcgagatc | gtcaaccgct | gctcctacac | 120 |
| cgtgtgggcg | gccgcctcca | aggcgacgc | cgccctggac | gccggcggcc | gccagctcaa | 180 |
| ctcgggagag | tcctggacca | tcaacgtaga | acccggcacc | aagggtggca | aaatctgggc | 240 |
| ccgcaccgac | tgctatttcg | acgacagcgg | ccgcggcatc | tgccggaccg | gcgactgcgg | 300 |
| cggcctcctc | cagtgcaagc | gcttcggccg | gccgccaccc | acgctggcgg | agttctcgct | 360 |
| caaccagtac | ggcaaggact | acatcgacat | ctccaacatc | aaaggcttca | acgtgccgat | 420 |
| ggacttcagc | ccgaccacgc | gcggctgccg | cggggtgcgg | tgcgccgccg | acatcgtggg | 480 |
| gcagtgcccg | gcgaagctga | aggcgccggg | ggtggttgc | aacgatgcgt | gcaccgtgtt | 540 |
| ccagacgagc | gagtactgct | gcaccacggg | gaagtgcggg | ccgacggagt | actcgcgctt | 600 |
| cttcaagagg | ctttgcccgg | acgcgttcag | ttatgtcctg | acaagccaa | ccaccgtcac | 660 |
| ctgccccggc | agctccaact | acagggtcac | tttctgccct | actgcccttg | aacttgaaga | 720 |
| cgagtaagag | gatgaagacg | gacactgagg | atacgcaata | aaagaataag | atgataagca | 780 |
| attatatcaa | taaaaagggt | acgtggttta | cgtcgagaag | gcatcagctt | gggaggaaaa | 840 |
| gtgttataaa | atatgtgtgt | ggggattggc | taattaaact | tgtaaaatat | aaataaaagt | 900 |
| tctccgtttt | gaggtgtgcc | tgcagtcatg | tttgacagct | tatcatcgat | aagcttggat | 960 |
| cc | | | | | | 962 |

<210> SEQ ID NO 2
<211> LENGTH: 13818
<212> TYPE: DNA
<213> ORGANISM: ARTIFICIAL SEQUENCE
<220> FEATURE:
<223> OTHER INFORMATION: Binary vector for plant transformation via
      Agrobacterium tumefaciens

<400> SEQUENCE: 2

| | | | | | | |
|---|---|---|---|---|---|---|
| tgagcgtcgc | aaaggcgctc | ggtcttgcct | tgctcgtcgg | tgatgtactt | caccagctcc | 60 |
| gcgaagtcgc | tcttcttgat | ggagcgcatg | gggacgtgct | tggcaatcac | gcgcaccccc | 120 |
| cggccgtttt | agcggctaaa | aaagtcatgg | ctctgccctc | gggcggacca | cgcccatcat | 180 |
| gaccttgcca | agctcgtcct | gcttctcttc | gatcttcgcc | agcagggcga | ggatcgtggc | 240 |
| atcaccgaac | cgcgccgtgc | gcgggtcgtc | ggtgagccag | agtttcagca | ggccgcccag | 300 |
| gcggcccagg | tcgccattga | tgcgggccag | ctcgcggacg | tgctcatagt | ccacgacgcc | 360 |
| cgtgattttg | tagccctggc | cgacggccag | caggtaggcc | gacaggctca | tgccggccgc | 420 |
| cgccgccttt | tcctcaatcg | ctcttcgttc | gtctggaagg | cagtacacct | tgataggtgg | 480 |
| gctgcccttc | ctggttggct | tggtttcatc | agccatccgc | ttgccctcat | ctgttacgcc | 540 |
| ggcggtagcc | ggccagcctc | gcagagcagg | attcccgttg | agcaccgcca | ggtgcgaata | 600 |
| agggacagtg | aagaaggaac | acccgctcgc | gggtgggcct | acttcaccta | tcctgcccgg | 660 |

```
ctgacgccgt tggatacacc aaggaaagtc tacacgaacc ctttggcaaa atcctgtata    720
tcgtgcgaaa aaggatggat ataccgaaaa aatcgctata atgaccccga agcagggtta    780
tgcagcggaa aagcgccacg cttcccgaag ggagaaaggc ggacaggtat ccggtaagcg    840
gcagggtcgg aacaggagag cgcacgaggg agcttccagg gggaaacgcc tggtatcttt    900
atagtcctgt cgggtttcgc cacctctgac ttgagcgtcg attttgtga tgctcgtcag     960 gggggcggag cctatggaaa aacgccagca acgcggcctt tttacggttc ctggcctttt   1020
gctggccttt tgctcacatg ttctttcctg cgttatcccc tgattctgtg gataaccgta   1080
ttaccgcctt tgagtgagct gataccgctc gccgcagccg aacgaccgag cgcagcgagt   1140
cagtgagcga ggaagcggaa gagcgccaga aggccgccag agaggccgag cgcggccgtg   1200
aggcttggac gctagggcag ggcatgaaaa agcccgtagc gggctgctac gggcgtctga   1260
cgcggtggaa aggggggagg gatgttgtct acatggctct gctgtagtga gtggggttgcg   1320 ctccggcagc ggtcctgatc aatcgtcacc ctttctcggt ccttcaacgt tcctgacaac   1380
gagcctcctt ttcgccaatc catcgacaat caccgcgagt ccctgctcga acgctgcgtc   1440
cggaccggct tcgtcgaagg cgtctatcgc ggcccgcaac agcggcgaga gcggagcctg   1500
ttcaacggtg ccgccgcgct cgccggcatc gctgtcgccg gcctgctcct caagcacggc   1560
cccaacagtg aagtagctga ttgtcatcag cgcattgacg gcgtcccgg  ccgaaaaacc   1620 cgcctcgcag aggaagcgaa gctgcgcgtc ggccgttcc  atctgcggtg cgcccggtcg   1680
cgtgccggca tggatgcgcg cgccatcgcg gtaggcgagc agcgcctgcc tgaagctgcg   1740
ggcattcccg atcagaaatg agcgccagtc gtcgtcggct ctcggcaccg aatgcgtatg   1800
attctccgcc agcatggctt cggccagtgc gtcgagcagc gcccgcttgt tcctgaagtg   1860
ccagtaaagc gccggctgct gaaccccccaa ccgttccgcc agtttgcgtg tcgtcagacc   1920
gtctacgccg acctcgttca acaggtccag ggcggcacgg atcactgtat tcggctgcaa   1980
ctttgtcatg cttgacactt tatcactgat aaacataata tgtccaccaa cttatcagtg   2040
ataaagaatc cgcgcgttca atcggaccag cggaggctgg tccggaggcc agacgtgaaa   2100
cccaacatac ccctgatcgt aattctgagc actgtcgcgc tcgacgctgt cggcatcggc   2160
ctgattatgc cggtgctgcc gggcctcctg cgcgatctgg ttcactcgaa cgacgtcacc   2220
gcccactatg gcattctgct ggcgctgtat gcgttggtgc aatttgcctg cgcacctgtg   2280
ctgggcgcgc tgtcggatcg tttcgggcgg cggccaatct tgctcgtctc gctggccggc   2340
gccagatctg gggaaccctg tggttggcat gcacatacaa atggacgaac ggataaacct   2400
tttcacgccc ttttaaatat ccgattattc taataaacgc tctttttctct taggtttacc   2460 cgccaatata tcctgtcaaa cactgatagt ttaaactgaa ggcgggaaac gacaatctga   2520
tcatgagcgg agaattaagg gagtcacgtt atgaccccccg ccgatgacgc gggacaagcc   2580
gttttacgtt tggaactgac agaaccgcaa cgttgaagga gccactcagc cgcgggtttc   2640
tggagtttaa tgagctaagc acatacgtca gaaaccatta ttgcgcgttc aaaagtcgcc   2700
taaggtcact atcagctagc aaatatttct tgtcaaaaat gctccactga cgttccataa   2760
attcccctcg gtatccaatt agagtctcat attcactctc aatccaaata atctgcaccg   2820
gatctggatc gtttcgcatg attgaacaag atggattgca cgcaggttct ccggccgctt   2880
gggtggagag gctattcggc tatgactggg cacaacagac aatcggctgc tctgatgccg   2940
ccgtgttccg gctgtcagcg cagggggcgcc cggttctttt tgtcaagacc gacctgtccg   3000
gtgccctgaa tgaactgcag gacgaggcag cgcggctatc gtggctggcc acgacgggcg   3060
```

```
ttccttgcgc agctgtgctc gacgttgtca ctgaagcggg aagggactgg ctgctattgg    3120
gcgaagtgcc ggggcaggat ctcctgtcat ctcaccttgc tcctgccgag aaagtatcca    3180
tcatggctga tgcaatgcgg cggctgcata cgcttgatcc ggctacctgc ccattcgacc    3240
accaagcgaa acatcgcatc gagcgagcac gtactcggat ggaagccggt cttgtcgatc    3300
aggatgatct ggacgaagag catcaggggc tcgcgccagc cgaactgttc gccaggctca    3360
aggcgcgcat gcccgacggc gatgatctcg tcgtgaccca tggcgatgcc tgcttgccga    3420
atatcatggt ggaaaatggc cgcttttctg gattcatcga ctgtggccgg ctgggtgtgg    3480
cggaccgcta tcaggacata gcgttggcta cccgtgatat tgctgaagag cttggcggcg    3540
aatgggctga ccgcttcctc gtgctttacg gtatcgccgc tcccgattcg cagcgcatcg    3600
ccttctatcg ccttcttgac gagttcttct gagcgggact ctggggttcg aaatgaccga    3660
ccaagcgacg cccaacctgc catcacgaga tttcgattcc accgccgcct tctatgaaag    3720
gttgggcttc ggaatcgttt tccgggacgc cggctgatg atcctccagc gcggggatct    3780
catgctggag ttcttcgccc acgggatctc tgcggaacag gcggtcgaag gtgccgatat    3840
cattacgaca gcaacggccg acaagcacaa cgccacgatc ctgagcgaca atatgatcgg    3900
gcccggcgtc cacatcaacg gcgtcggcgg cgactgccca ggcaagaccg agatgcaccg    3960
cgatatcttg ctgcgttcgg atattttcgt ggagttcccg ccacagaccc ggatgatccc    4020
cgatcgttca aacatttggc aataaagttt cttaagattg aatcctgttg ccggtcttgc    4080
gatgattatc atataatttc tgttgaatta cgttaagcat gtaataatta acatgtaatg    4140
catgacgtta tttatgagat gggtttttat gattagagtc ccgcaattat acatttaata    4200
cgcgatagaa aacaaaatat agcgcgcaaa ctaggataaa ttatcgcgcg cggtgtcatc    4260
tatgttacta gatcgggcct cctgtcaatg ctggcggcgg ctctggtggt ggttctggtg    4320
gcggctctga gggtggtggc tctgagggtg gcggttctga gggtggcggc tctgagggag    4380
gcggttccgg tggtggctct ggttccggtg attttgatta tgaaagatg gcaaacgcta    4440
ataaggggc tatgaccgaa aatgccgatg aaaacgcgct acagtctgac gctaaaggca    4500
aacttgattc tgtcgctact gattacggtg ctgctatcga tggtttcatt ggtgacgttt    4560
ccggccttgc taatggtaat ggtgctactg gtgattttgc tggctctaat tcccaaatgg    4620
ctcaagtcgg tgacggtgat aattcacctt taatgaataa tttccgtcaa tatttacctt    4680
ccctccctca atcggttgaa tgtcgccctt ttgtctttgg cccaatacgc aaaccgcctc    4740
tccccgcgcg ttggccgatt cattaatgca gctggcacga caggtttccc gactggaaag    4800
cgggcagtga gcgcaacgca attaatgtga gttagctcac tcattaggca ccccaggctt    4860
tacactttat gcttccggct cgtatgttgt gtggaattgt gagcggataa caatttcaca    4920
caggaaacag ctatgaccat gattacgcca agcttgcatg cctgcaggtc cccagattag    4980
ccttttcaat ttcagaaaga atgctaaccc acagatggtt agagaggctt acgcagcagg    5040
tctcatcaag acgatctacc cgagcaataa tctccaggaa atcaaatacc ttcccaagaa    5100
ggttaaagat gcagtcaaaa gattcaggac taactgcatc aagaacacag agaaagatat    5160
atttctcaag atcagaagta ctattccagt atggacgatt caaggcttgc ttcacaaacc    5220
aaggcaagta atagagattg gagtctctaa aaggtagtt cccactgaat caaaggccat    5280
ggagtcaaag attcaaatag aggacctaac agaactcgcc gtaaagactg gcgaacagtt    5340
catacagagt ctcttacgac tcaatgacaa gaagaaaatc ttcgtcaaca tggtggagca    5400
cgacacactt gtctactcca aaaatatcaa agatacagtc tcagaagacc aaagggcaat    5460
```

```
tgagactttt caacaaaggg taatatccgg aaacctcctc ggattccatt gcccagctat   5520
ctgtcacttt attgtgaaga tagtggaaaa ggaaggtggc tcctacaaat gccatcattg   5580
cgataaagga aaggccatcg ttgaagatgc ctctgccgac agtggtccca agatggacc    5640
cccacccacg aggagcatcg tggaaaaaga agacgttcca accacgtctt caaagcaagt   5700
ggattgatgt gatatctcca ctgacgtaag ggatgacgca caatcccact atccttcgca   5760
agacccttcc tctatataag gaagttcatt tcatttggag agaacacggg ggactctaga   5820
ctcgaggaat tctatggccg ccaccacttg cttcttcttc ctcttcccct tcctcctcct   5880
cctcacgctc tcccgcgctg ccaccttcga gatcgtcaac cgctgctcct acaccgtgtg   5940
ggcggccgcc tccaaaggcg acgccgccct ggacgccggc ggccgccagc tcaactcggg   6000
agagtcctgg accatcaacg tagaacccgg caccaagggt ggcaaaatct gggcccgcac   6060
cgactgctat ttcgacgaca gcggccgcgc catctgccgg accggcgact gcggcggcct   6120
cctccagtgc aagcgcttcg gccggccgcc caccacgctg gcggagttct cgctcaacca   6180
gtacggcaag gactacatcg acatctccaa catcaaaggc ttcaacgtgc cgatggactt   6240
cagcccgacc acgcgcggct gccgcggggt gcggtgcgcc gccgacatcg tggggcagtg   6300
cccggcgaag ctgaaggcgc cgggggggtgg ttgcaacgat gcgtgcaccg tgttccagac   6360
gagcgagtac tgctgcacca cggggaagtg cgggccgacg gagtactcgc gcttcttcaa   6420
gaggctttgc ccggacgcgt tcagttatgt cctggacaag ccaaccaccg tcacctgccc   6480
cggcagctcc aactcagggg tcactttctg ccctactgcc cttgaacttg aagacgagta   6540
agaggatgaa gacggacact gaggatacgc aataaaagaa taagatgata agcaattata   6600
tcaataaaaa gggtacgtgg tttacgtcga gaaggcatca gcttgggagg aaaagtgtta   6660
taaaatatgt gtgtggggat tggctaatta aacttgtaaa atataaataa aagttctccg   6720
ttttgaggtg tgcctgcagt catgtttgac agcttatcat cgataagctt ggatccgaat   6780
tccccgatc gttcaaacat ttggcaataa agtttcttaa gattgaatcc tgttgccggt   6840
cttgcgatga ttatcatata atttctgttg aattacgtta agcatgtaat aattaacatg   6900
taatgcatga cgttatttat gagatggggtt tttatgatta gagtcccgca attatacatt   6960
taatacgcga tagaaaacaa aatatagcgc gcaaactagg ataaattatc gcgcgcggtg   7020
tcatctatgt tactagatcg ggaattcact ggccgtcgtt ttacaacgtc gtgactggga   7080
aaaccctggc gttacccaac ttaatcgcct tgcagcacat ccccctttcg ccagctggcg   7140
taatagcgaa gaggcccgca ccgatcgccc ttcccaacag ttgcgcagcc tgaatggcgc   7200
ccgctccttt cgctttcttc ccttcctttc tcgccacgtt cgccggcttt ccccgtcaag   7260
ctctaaatcg ggggctccct ttagggttcc gatttagtgc tttacggcac ctcgacccca   7320
aaaaacttga tttgggtgat ggttcacgta gtgggccatc gccctgatag acggtttttc   7380
gccctttgac gttggagtcc acgttcttta atagtggact cttgttccaa actggaacaa   7440
cactcaaccc tatctcgggc tattcttttg atttataagg gattttgccg atttcggaac   7500
caccatcaaa caggattttc gcctgctggg gcaaaccagc gtggaccgct tgctgcaact   7560
ctctcagggc caggcggtga agggcaatca gctgttgccc gtctcactgg tgaaaagaaa   7620
aaccacccca gtacattaaa aacgtccgca atgtgttatt aagttgtcta agcgtcaatt   7680
tgtttacacc acaatatatc ctgccaccag ccagccaaca gctccccgac cggcagctcg   7740
gcacaaaatc accactcgat acaggcagcc catcagtccg ggacggcgtc agcgggagag   7800
ccgttgtaag gcggcagact ttgctcatgt taccgatgct attcggaaga acggcaacta   7860
```

```
agctgccggg tttgaaacac ggatgatctc gcggagggta gcatgttgat tgtaacgatg   7920
acagagcgtt gctgcctgtg atcaaatatc atctccctcg cagagatccg aattatcagc   7980
cttcttattc atttctcgct taaccgtgac aggctgtcga tcttgagaac tatgccgaca   8040
taataggaaa tcgctggata aagccgctga ggaagctgag tggcgctatt tctttagaag   8100
tgaacgttga cgatatcaac tcccctatcc attgctcacc gaatggtaca ggtcggggac   8160
ccgaagttcc gactgtcggc ctgatgcatc cccggctgat cgaccccaga tctgggctg    8220 agaaagccca gtaaggaaac aactgtaggt tcgagtcgcg agatccccg gaaccaaagg    8280 aagtaggtta aacccgctcc gatcaggccg agccacgcca ggccgagaac attggttcct   8340
gtaggcatcg ggattggcgg atcaaacact aaagctactg gaacgagcag aagtcctccg   8400
gccgccagtt gccaggcggt aaaggtgagc agaggcacgg gaggttgcca cttgcgggtc   8460
agcacggttc cgaacgccat ggaaaccgcc cccgccaggc ccgctgcgac gccgacagga   8520
tctagcgctg cgtttggtgt caacaccaac agcgccacgc ccgcagttcc gcaaatagcc   8580
cccaggaccg ccatcaatcg tatcgggcta cctagcagag cggcagagat gaacacgacc   8640
atcagcggct gcacagcgcc taccgtcgcc gcgaccccgc ccggcaggcg gtagaccgaa   8700
ataaacaaca agctccagaa tagcgaaata ttaagtgcgc cgaggatgaa gatgcgcatc   8760
caccagattc ccgttggaat ctgtcggacg atcatcacga gcaataaacc cgccggcaac   8820
gcccgcagca gcataccggc gacccctcgg cctcgctgtt cgggctccac gaaaacgccg   8880
gacagatgcg ccttgtgagc gtccttgggg ccgtcctcct gtttgaagac cgacagccca   8940
atgatctcgc cgtcgatgta ggcgccgaat gccacggcat ctcgcaaccg ttcagcgaac   9000
gcctccatgg gcttttttctc ctcgtgctcg taaacggacc cgaacatctc tggagctttc   9060
ttcagggccg acaatcggat ctcgcggaaa tcctgcacgt cggccgctcc aagccgtcga   9120
atctgagcct taatcacaat tgtcaatttt aatcctctgt ttatcggcag ttcgtagagc   9180
gcgccgtgcg tcccgagcga tactgagcga agcaagtgcg tcgagcagtg cccgcttgtt   9240
cctgaaatgc cagtaaagcg ctggctgctg aaccccagc cggaactgac cccacaaggc   9300
cctagcgttt gcaatgcacc aggtcatcat tgacccaggc gtgttccacc aggccgctgc   9360
ctcgcaactc ttcgcaggct tcgccgacct gctcgcgcca cttcttcacg cgggtggaat   9420
ccgatccgca catgaggcgg aaggtttcca gcttgagcgg gtacggctcc cggtgcgagc   9480
tgaaatagtc gaacatccgt cgggccgtcg gcgacagctt gcggtacttc tcccatatga   9540
atttcgtgta gtggtcgcca gcaaacagca cgacgatttc ctcgtcgatc aggacctggc   9600
aacgggacgt tttcttgcca cggtccagga cgcggaagcg gtgcagcagc gacaccgatt   9660
ccaggtgccc aacgcggtcg gacgtgaagc ccatcgccgt cgcctgtagg cgcgacaggc   9720
attcctcggc cttcgtgtaa taccggccat tgatcgacca gcccaggtcc tggcaaagct   9780
cgtagaacgt gaaggtgatc ggctcgccga taggggtgcg cttcgcgtac tccaacacct   9840
gctgccacac cagttcgtca tcgtcggccc gcagctcgac gccggtgtag gtgatcttca   9900
cgtccttgtt gacgtggaaa atgaccttgt tttgcagcgc ctcgcgcggg attttcttgt   9960
tgcgcgtggt gaacagggca gagcgggccg tgtcgtttgg catcgctcgc atcgtgtccg   10020
gccacggcgc aatatcgaac aaggaaagct gcatttcctt gatctgctgc ttcgtgtgtt   10080
tcagcaacgc ggcctgcttg gcctcgctga cctgttttgc caggtcctcg ccggcggttt   10140
ttcgcttctt ggtcgtcata gttcctcgcg tgtcgatggt catcgacttc gccaaacctg   10200
ccgcctcctg ttcgagacga cgcgaacgct ccacggcggc cgatggcgcg gcagggcag   10260
```

```
ggggagccag ttgcacgctg tcgcgctcga tcttggccgt agcttgctgg accatcgagc   10320
cgacggactg gaaggtttcg cggggcgcac gcatgacggt gcggcttgcg atggtttcgg   10380
catcctcggc ggaaaacccc gcgtcgatca gttcttgcct gtatgccttc cggtcaaacg   10440
tccgattcat tcaccctcct tgcgggattg ccccgactca cgccggggca atgtgccctt   10500
attcctgatt tgacccgcct ggtgccttgg tgtccagata tccaccttta tcggcaatga   10560
agtcggtccc gtagaccgtc tggccgtcct tctcgtactt ggtattccga atcttgccct   10620
gcacgaatac cagcgacccc ttgcccaaat acttgccgtg ggcctcggcc tgagagccaa   10680
aacacttgat gcggaagaag tcggtgcgct cctgcttgtc gccggcatcg ttgcgccaca   10740
tctaggtact aaaacaattc atccagtaaa atataatatt ttattttctc ccaatcaggc   10800
ttgatcccca gtaagtcaaa aaatagctcg acatactgtt cttccccgat atcctccctg   10860
atcgaccgga cgcagaaggc aatgtcatac cacttgtccg ccctgccgct tctcccaaga   10920
tcaataaagc cacttacttt gccatctttc acaaagatgt tgctgtctcc caggtcgccg   10980
tgggaaaaga caagttcctc ttcgggcttt tccgtcttta aaaaatcata cagctcgcgc   11040
ggatctttaa atggagtgtc ttcttcccag ttttcgcaat ccacatcggc cagatcgtta   11100
ttcagtaagt aatccaattc ggctaagcgg ctgtctaagc tattcgtata gggacaatcc   11160
gatatgtcga tggagtgaaa gagcctgatg cactccgcat acagtcgat aatcttttca    11220 gggctttgtt catcttcata ctcttccgag caaaggacgc catcggcctc actcatgagc   11280
agattgctcc agccatcatg ccgttcaaag tgcaggacct tggaacagg cagctttcct    11340 tccagccata gcatcatgtc cttttcccgt tccacatcat aggtggtccc tttataccgg   11400
ctgtccgtca ttttttaaata taggttttca ttttctccca ccagcttata tacccttagca  11460 ggagacattc cttccgtatc ttttacgcag cggtattttt cgatcagttt tttcaattcc   11520
ggtgatattc tcattttagc catttattat ttccttcctc ttttctacag tatttaaaga   11580
taccccaaga agctaattat aacaagacga actccaattc actgttcctt gcattctaaa   11640
accttaaata ccagaaaaca gctttttcaa agttgttttc aaagttggcg tataacatag   11700
tatcgacgga gccgattttg aaaccacaat tatgggtgat gctgccaact tactgattta   11760
gtgtatgatg gtgtttttga ggtgctccag tggcttctgt gtctatcagc tgtccctcct   11820
gttcagctac tgacggggtg gtgcgtaacg gcaaaagcac cgccggacat cagcgctatc   11880
tctgctctca ctgccgtaaa acatggcaac tgcagttcac ttacaccgct tctcaacccg   11940
gtacgcacca gaaaatcatt gatatggcca tgaatggcgt tggatgccgg gcaacagccc   12000
gcattatggg cgttggcctc aacacgattt tacgtcactt aaaaaactca ggccgcagtc   12060
ggtaacctcg cgcatacagc cgggcagtga cgtcatcgtc tgcgcggaaa tggacgaaca   12120
gtggggctat gtcggggcta aatcgcgcca gcgctggctg ttttacgcgt atgacagtct   12180
ccggaagacg gttgttgcgc acgtattcgg tgaacgcact atgcgacgc tggggcgtct    12240 tatgagcctg ctgtcaccct ttgacgtggt gatatgatg acggatggct ggccgctgta    12300
tgaatcccgc ctgaagggaa agctgcacgt aatcagcaag cgatatacgc agcgaattga   12360
gcggcataac ctgaatctga ggcagcacct ggcacggctg gacggaagt cgctgtcgtt    12420 ctcaaaatcg gtggagctgc atgacaaagt catcgggcat tatctgaaca taaaacacta   12480
tcaataagtt ggagtcatta cccaattatg atagaattta caagctataa ggttattgtc   12540
ctgggtttca agcattagtc catgcaagtt tttatgcttt gcccattcta tagatatatt   12600
gataagcgcg ctgcctatgc cttgcccct gaaatcctta catacggcga tatcttctat    12660
```

```
ataaaagata tattatctta tcagtattgt caatatattc aaggcaatct gcctcctcat    12720
cctcttcatc ctcttcgtct tggtagcttt ttaaatatgg cgcttcatag agtaattctg    12780
taaaggtcca attctcgttt tcatacctcg gtataatctt acctatcacc tcaaatggtt    12840
cgctgggttt atcgcacccc cgaacacgag cacggcaccc gcgaccacta tgccaagaat    12900
gcccaaggta aaaattgccg gccccgccat gaagtccgtg aatgcccga cggccgaagt     12960 gaagggcagg ccgccaccca ggccgccgcc ctcactgccc ggcacctggt cgctgaatgt    13020
cgatgccagc acctgcggca cgtcaatgct tccgggcgtc gcgctcgggc tgatcgccca    13080
tcccgttact gccccgatcc cggcaatggc aaggactgcc agcgctgcca tttttggggt    13140
gaggccgttc gcggccgagg ggcgcagccc ctgggggat gggaggcccg cgttagcggg      13200
ccgggagggt tcgagaaggg ggggcacccc ccttcggcgt gcgcggtcac gcgcacaggg    13260
cgcagccctg gttaaaaaca aggtttataa atattggttt aaaagcaggt taaaagacag    13320
gttagcggtg gccgaaaaac gggcggaaac ccttgcaaat gctggatttt ctgcctgtgg    13380
acagcccctc aaatgtcaat aggtgcgccc ctcatctgtc agcactctgc ccctcaagtg    13440
tcaaggatcg cgcccctcat ctgtcagtag tcgcgcccct caagtgtcaa taccgcaggg    13500
cacttatccc caggcttgtc cacatcatct gtgggaaact cgcgtaaaat caggcgtttt    13560
cgccgatttg cgaggctggc cagctccacg tcgccggccg aaatcgagcc tgcccctcat    13620
ctgtcaacgc cgcgccgggt gagtcggccc ctcaagtgtc aacgtccgcc cctcatctgt    13680
cagtgagggc caagttttcc gcgaggtatc cacaacgccg gcggccgcgg tgtctcgcac    13740
acggcttcga cggcgtttct ggcgcgtttg cagggccata gacggccgcc agcccagcgg    13800
cgagggcaac cagcccgg                                                  13818

<210> SEQ ID NO 3
<211> LENGTH: 5544
<212> TYPE: DNA
<213> ORGANISM: ARTIFICIAL SEQUENCE
<220> FEATURE:
<223> OTHER INFORMATION: Expression vector containing a fragment coding
      for thaumatin II

<400> SEQUENCE: 3
ctgcagtcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct    240
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcctctacgc cggacgcatc gtggccggca tcaccggcgc    420
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt gcggcggcgg tgctcaacgg    600
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt tcgctggagc gcgacgatga tcggcctgtc    840
```

```
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
agaattggag ccaatcaatt cttgcggaga actgtgaatg cgcaaaccaa cccttggcag   1380
aacatatcca tcgcgtccgc catctccagc agccgcacgc ggcgcatctc gggcagcgtt   1440
gggtcctggc cacgggtgcg catgatcgtg ctcctgtcgt tgaggacccg gctaggctgg   1500
cggggttgcc ttactggtta gcagaatgaa tcaccgatac gcgagcgaac gtgaagcgac   1560
tgctgctgca aaacgtctgc gacctgagca caacatgaa tggtcttcgg tttccgtgtt   1620
tcgtaaagtc tggaaacgcg gaagtcagcg ccctgcacca ttatgttccg gatctgcatc   1680
gcaggatgct gctggctacc ctgtggaaca cctacatctg tattaacgaa gcgctggcat   1740
tgaccctgag tgattttct ctggtcccgc cgcatccata ccgccagttg tttaccctca   1800
caacgttcca gtaaccgggc atgttcatca tcagtaaccc gtatcgtgag catcctctct   1860
cgtttcatcg gtatcattac ccccatgaac agaaatcccc cttacacgga ggcatcagtg   1920
accaaacagg aaaaaaccgc ccttaacatg gcccgcttta tcagaagcca gacattaacg   1980
cttctggaga aactcaacga gctggacgcg gatgaacagg cagacatctg tgaatcgctt   2040
cacgaccacg ctgatgagct ttaccgcagc tgcctcgcgc gtttcggtga tgacggtgaa   2100
aacctctgac acatgcagct cccggagacg gtcacagctt gtctgtaagc ggatgccggg   2160
agcagacaag cccgtcaggg cgcgtcagcg ggtgttggcg ggtgtcgggg cgcagccatg   2220
acccagtcac gtagcgatag cggagtgtat actggcttaa ctatgcggca tcagagcaga   2280
ttgtactgag agtgcaccat atgcggtgtg aaataccgca cagatgcgta aggagaaaat   2340
accgcatcag gcgctcttcc gcttcctcgc tcactgactc gctgcgctcg gtcgttcggc   2400
tgcggcgagc ggtatcagct cactcaaagg cggtaatacg gttatccaca gaatcagggg   2460
ataacgcagg aaagaacatg tgagcaaaag gccagcaaaa ggccaggaac cgtaaaaagg   2520
ccgcgttgct ggcgtttttc cataggctcc gcccccctga cgagcatcac aaaaatcgac   2580
gctcaagtca gaggtggcga aacccgacag gactataaag ataccaggcg tttccccctg   2640
gaagctccct cgtgcgctct cctgttccga cccgccgct taccggatac ctgtccgcct   2700
ttctccttc gggaagcgtg gcgctttctc atagctcacg ctgtaggtat ctcagttcgg   2760
tgtaggtcgt tcgctccaag ctgggctgtg tgcacgaacc ccccgttcag cccgaccgct   2820
gcgccttatc cggtaactat cgtcttgagt ccaacccggt aagacacgac ttatcgccac   2880
tggcagcagc cactggtaac aggattagca gagcgaggta tgtaggcggt gctacagagt   2940
tcttgaagtg gtggcctaac tacggctaca ctagaaggac agtatttggt atctgcgctc   3000
tgctgaagcc agttaccttc ggaaaaagag ttggtagctc ttgatccggc aaacaaacca   3060
ccgctggtag cggtggtttt tttgtttgca agcagcagat tacgcgcaga aaaaaggat   3120
ctcaagaaga tcctttgatc ttttctacgg ggtctgacgc tcagtggaac gaaaactcac   3180
gttaagggat tttggtcatg agattatcaa aaaggatctt cacctagatc cttttaaatt   3240
```

```
aaaaatgaag ttttaaatca atctaaagta tatatgagta aacttggtct gacagttacc    3300
aatgcttaat cagtgaggca cctatctcag cgatctgtct atttcgttca tccatagttg    3360
cctgactccc cgtcgtgtag ataactacga tacgggaggg cttaccatct ggccccagtg    3420
ctgcaatgat accgcgagac ccacgctcac cggctccaga tttatcagca ataaaccagc    3480
cagccggaag ggccgagcgc agaagtggtc ctgcaacttt atccgcctcc atccagtcta    3540
ttaattgttg ccgggaagct agagtaagta gttcgccagt taatagtttg cgcaacgttg    3600
ttgccattgc tgcaggcatc gtggtgtcac gctcgtcgtt tggtatggct tcattcagct    3660
ccggttccca acgatcaagg cgagttacat gatcccccat gttgtgcaaa aaagcggtta    3720
gctccttcgg tcctccgatc gttgtcagaa gtaagttggc cgcagtgtta tcactcatgg    3780
ttatggcagc actgcataat tctcttactg tcatgccatc cgtaagatgc ttttctgtga    3840
ctggtgagta ctcaaccaag tcattctgag aatagtgtat gcggcgaccg agttgctctt    3900
gcccggcgtc aacacgggat aataccgcgc cacatagcag aactttaaaa gtgctcatca    3960
ttggaaaacg ttcttcgggg cgaaaactct caaggatctt accgctgttg agatccagtt    4020
cgatgtaacc cactcgtgca cccaactgat cttcagcatc ttttactttc accagcgttt    4080
ctgggtgagc aaaaacagga aggcaaaatg ccgcaaaaaa gggaataagg gcgacacgga    4140
aatgttgaat actcatactc ttcctttttc aatattattg aagcatttat cagggttatt    4200
gtctcatgag cggatacata tttgaatgta tttagaaaaa taaacaaata ggggttccgc    4260
gcacatttcc ccgaaaagtg ccacctgacg tctaagaaac cattattatc atgacattaa    4320
cctataaaaa taggcgtatc acgaggccct ttcgtcttca actcactcat taggcacccc    4380
aggctttaca ctttatgctt ccggctcgta taatgtgtgg aattgtgagc ggataacaat    4440
ttcacacagg aaacagctga tgccttcacc gcctggcctc cgttgagcca tctggatcgg    4500
cagcgttgtc ttcatcaacc ggaacgagca tgccggagag cagctcactc attaggcacc    4560
ccaggcttta cactttatgc ttccggctcg tataatgtgt ggaattgtga gcggataaca    4620
atttcacaca ggaaacagaa ttctatggcc gccaccactt gcttcttctt cctcttcccc    4680
ttcctcctcc tcctcacgct ctcccgcgct gccaccttcg agatcgtcaa ccgctgctcc    4740
tacaccgtgt gggcggccgc ctccaaaggc gacgccgccc tggacgccgg cggccgccag    4800
ctcaactcgg gagagtcctg gaccatcaac gtagaacccg gcaccaaggg tggcaaaatc    4860
tgggcccgca ccgactgcta tttcgacgac agcggccgcg catctgccg gaccggcgac    4920
tgcggcggcc tcctccagtg caagcgcttc ggccggccgc ccaccacgct ggcggagttc    4980
tcgctcaacc agtacggcaa ggactacatc gacatctcca acatcaaagg cttcaacgtg    5040
ccgatggact tcagcccgac cacgcgcggc tgccgcgggg tgcggtgcgc cgccgacatc    5100
gtggggcagt gcccggcgaa gctgaaggcg ccggggggtg gttgcaacga tgcgtgcacc    5160
gtgttccaga cgagcgagta ctgctgcacc acggggaagt gcgggccgac ggagtactcg    5220
cgcttcttca agaggctttg cccggacgcg ttcagttatg tcctggacaa gccaaccacc    5280
gtcacctgcc ccggcagctc caactacagg gtcactttct gccctactgc ccttgaactt    5340
gaagacgagt aagaggatga agacggacac tgaggatacg caataaaaga ataagatgat    5400
aagcaattat atcaataaaa agggtacgtg gtttacgtcg agaaggcatc agcttgggag    5460
gaaaagtgtt ataaaatatg tgtgtgggga ttggctaatt aaacttgtaa aatataaata    5520
aaagttctcc gttttgaggt gtgc                                           5544
```

<210> SEQ ID NO 4

<211> LENGTH: 3614
<212> TYPE: DNA
<213> ORGANISM: ARTIFICIAL SEQUENCE
<220> FEATURE:
<223> OTHER INFORMATION: Intermediary cloning vector based on pUC19 containing synthetic MCS

<400> SEQUENCE: 4

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgcatg | ctctagactc | gaggaattct | 420 |
| atggccgcca | ccacttgctt | cttcttcctc | ttccccttcc | tcctcctcct | cacgctctcc | 480 |
| cgcgctgcca | ccttcgagat | cgtcaaccgc | tgctcctaca | ccgtgtgggc | ggccgcctcc | 540 |
| aaaggcgacg | ccgccctgga | cgccggcggc | cgccagctca | actcgggaga | gtcctggacc | 600 |
| atcaacgtag | aacccggcac | caagggtggc | aaaatctggg | cccgcaccga | ctgctatttc | 660 |
| gacgacagcg | gccgcggcat | ctgccggacc | ggcgactgcg | gcggcctcct | ccagtgcaag | 720 |
| cgcttcggcc | ggccgcccac | cacgctggcg | gagttctcgc | tcaaccagta | cggcaaggac | 780 |
| tacatcgaca | tctccaacat | caaaggcttc | aacgtgccga | tggacttcag | cccgaccacg | 840 |
| cgcggctgcc | gcggggtgcg | gtgcgccgcc | gacatcgtgg | ggcagtgccc | ggcgaagctg | 900 |
| aaggcgccgg | ggggtggttg | caacgatgcg | tgcaccgtgt | tccagacgag | cgagtactgc | 960 |
| tgcaccacgg | ggaagtgcgg | gccgacggag | tactcgcgct | tcttcaagag | gctttgcccg | 1020 |
| gacgcgttca | gttatgtcct | ggacaagcca | accaccgtca | cctgccccgg | cagctccaac | 1080 |
| tacagggtca | ctttctgccc | tactgcccct | gaacttgaag | acgagtaaga | ggatgaagac | 1140 |
| ggacactgag | gatacgcaat | aaaagaataa | gatgataagc | aattatatca | ataaaagggg | 1200 |
| tacgtggttt | acgtcgagaa | ggcatcagct | tgggaggaaa | agtgttataa | aatatgtgtg | 1260 |
| tggggattgg | ctaattaaac | ttgtaaaata | taaataaaag | ttctccgttt | tgaggtgtgc | 1320 |
| ctgcagtcat | gtttgacagc | ttatcatcga | taagcttgga | tccccatcgt | tatggccggg | 1380 |
| ggcgtaatca | tggtcatagc | tgtttcctgt | gtgaaattgt | tatccgctca | caattccaca | 1440 |
| caacatacga | gccggaagca | taaagtgtaa | agcctggggt | gcctaatgag | tgagctaact | 1500 |
| cacattaatt | gcgttgcgct | cactgcccgc | tttccagtcg | ggaaacctgt | cgtgccagct | 1560 |
| gcattaatga | atcggccaac | gcgcggggag | aggcggtttg | cgtattgggc | gctcttccgc | 1620 |
| ttcctcgctc | actgactcgc | tgcgctcggt | cgttcggctg | cggcgagcgg | tatcagctca | 1680 |
| ctcaaaggcg | gtaatacggt | tatccacaga | atcagggat | aacgcaggaa | agaacatgtg | 1740 |
| agcaaaaggc | cagcaaaagg | ccaggaaccg | taaaaaggcc | gcgttgctgg | cgttttccca | 1800 |
| taggctccgc | ccccctgacg | agcatcacaa | aaatcgacgc | tcaagtcaga | ggtggcgaaa | 1860 |
| cccgacagga | ctataaagat | accaggcgtt | tccccctgga | agctccctcg | tgcgctctcc | 1920 |
| tgttccgacc | ctgccgctta | ccggatacct | gtccgccttt | ctcccttcgg | gaagcgtggc | 1980 |
| gctttctcaa | tgctcacgct | gtaggtatct | cagttcggtg | taggtcgttc | gctccaagct | 2040 |
| gggctgtgtg | cacgaacccc | ccgttcagcc | cgaccgctgc | gccttatccg | gtaactatcg | 2100 |
| tcttgagtcc | aacccggtaa | gacacgactt | atcgccactg | gcagcagcca | ctggtaacag | 2160 |

```
gattagcaga gcgaggtatg taggcggtgc tacagagttc ttgaagtggt ggcctaacta    2220
cggctacact agaaggacag tatttggtat ctgcgctctg ctgaagccag ttaccttcgg    2280
aaaaagagtt ggtagctctt gatccggcaa acaaaccacc gctggtagcg gtggttttt    2340 tgtttgcaag cagcagatta cgcgcagaaa aaaaggatct caagaagatc ctttgatctt    2400
ttctacgggg tctgacgctc agtggaacga aaactcacgt taagggatt tggtcatgag     2460 attatcaaaa aggatcttca cctagatcct tttaaattaa aaatgaagtt ttaaatcaat    2520
ctaaagtata tatgagtaaa cttggtctga cagttaccaa tgcttaatca gtgaggcacc    2580
tatctcagcg atctgtctat ttcgttcatc catagttgcc tgactcccg tcgtgtagat     2640 aactacgata cgggagggct taccatctgg ccccagtgct gcaatgatac cgcgagaccc    2700
acgctcaccg gctccagatt tatcagcaat aaaccagcca gccggaaggg ccgagcgcag    2760
aagtggtcct gcaactttat ccgcctccat ccagtctatt aattgttgcc gggaagctag    2820
agtaagtagt tcgccagtta atagtttgcg caacgttgtt gccattgcta caggcatcgt    2880
ggtgtcacgc tcgtcgtttg gtatggcttc attcagctcc ggttcccaac gatcaaggcg    2940
agttacatga tcccccatgt tgtgcaaaaa agcggttagc tccttcggtc ctccgatcgt    3000
tgtcagaagt aagttggccg cagtgttatc actcatggtt atggcagcac tgcataattc    3060
tcttactgtc atgccatccg taagatgctt ttctgtgact ggtgagtact caaccaagtc    3120
attctgagaa tagtgtatgc ggcgaccgag ttgctcttgc ccggcgtcaa tacgggataa    3180
taccgcgcca catagcagaa ctttaaaagt gctcatcatt ggaaaacgtt cttcggggcg    3240
aaaactctca aggatcttac cgctgttgag atccagttcg atgtaaccca ctcgtgcacc    3300
caactgatct tcagcatctt ttactttcac cagcgtttct gggtgagcaa aacaggaag     3360 gcaaaatgcc gcaaaaaagg gaataagggc gacacggaaa tgttgaatac tcatactctt    3420
cctttttcaa tattattgaa gcatttatca gggttattgt ctcatgagcg gatacatatt    3480
tgaatgtatt tagaaaaata aacaaatagg ggttccgcgc acatttcccc gaaaagtgcc    3540
acctgacgtc taagaaacca ttattatcat gacattaacc tataaaaata ggcgtatcac    3600
gaggcccttt cgtc                                                      3614
```

METHOD FOR PRODUCING A TRANSGENIC PLANT WITH THE AID OF *AGROBACTERIUM THUMEFACIENS*

FIELD OF THE INVENTION

The present invention relates to the genetic engineering of plants and can be used for producing transgenic plants with desired properties.

DESCRIPTION OF THE PRIOR ART

The main damage to farm crops is caused by viral, bacterial and fungal pathogens, this damage materially exceeding that caused by insects and other pests taken together. In their turn, pathogenic fungi hold the first place in their harmfulness among other pathogens.

For example, effective cultivation of strawberry is limited by several diseases: red stele (caused by (*Phytophthora fragariae*), verticillaceous wilt (*Verticillium alboatrum*), leaf spot (*Mycosphaerella fragariae*), leaf blight (*Diplocarpon aerliana*), leaf roll (*Dendrophoma obscurans*), grey mold (*Botrytis cinerea*), powdery mildew (*Sphaerotheca humuili*) and others. Fungi which cause plant diseases not only affect the growth and development of plant organism, but often lower the productivity of cultivated plants.

In present-day agriculture effective control of fungal pathogens is achieved by a comprehensive approach. On the one hand, conventional selection methods are used to develop new varieties which display an enhanced resistance to definite races of fungi. But the development of one variety in such a way takes on an average abut 10 years. During this period of time pathogens often manage to mutate, and the new variety loses resistance and rapidly becomes obsolete. An alternative approach is offered by genetic engineering. A method of genetic transformation of plants makes it possible to transfer into plants separate disease resistance genes and obtain during a short period of time-plants with enhanced resistance to a wide range of phytopathogens.

Producing transgenic plants with an enhanced resistance usually encounters the problems of reproducibility of the known methods and the problems of producing plants with a low level of somaclonal variability.

Publications are known, devoted to optimizing the method of transformation of garden strawberry, developed by James et al (1990) and Nehra et al. (1990). In the method of transformation there were varied: 1) the composition of the mineral and/or hormonal medium for the regeneration and selection of transformants, 2) the type and concentration of the selective agent, 3) the genotype of the variety, 4) the type of the strain and the vector construct, 5) the type and concentration of carbohydrates, 6) the type of the explant (leaves, petiole, tendril segments, meristem).

Du Plessis et al. (1999) have modified the method of agrobacterial-transformation by substituting 6-benzylaminopurine in the selection and transformation medium by the synthetic growth regulator tidiazuron. It proved to be a more effective growth regulator for strawberry. Instead of the agrobacterial strain LBA4404 the authors began to use C58/PGW2260. The developed method suffers from a serious disadvantage: a very high frequency of somaclonal variations among transformants.

Dier et al. (2001) have shown that the substitution of sucrose by glucose in the media for the multiplication, co-cultivation, selection and regeneration of transformants essentially increases the frequency of regeneration of transgenic shoots. A solution is known, in which the authors make an attempt to decrease the frequency of somaclonal variations by substituting sucrose by maltose (Stuart et al, U.S. Pat. No. 4,801,545, 1989).

Mathews et al. (1998) have shown that the concentration and type of the selective agent in the culture medium have a very significant effect on the process of regeneration of transgenic shoots. The duration of cultivation on a selective medium is also of importance. Modification of the selection system made it possible to produce pure, non-chimeric lines consisting of transgenic cells only.

Dolgov et al. (1999), using the method described in James et al. (1990) and Nehra et al. (1990), developed for the Redcoat variety, produced a transgenic plant of garden strawberry of the Feyerverk variety. The effectiveness of the transformation method for the Fireworks variety turned out to be less than 1%, while for the Redcoat variety the effectiveness of the developed method was 6.5%.

De Mesa et al. (2000) have modified the method of genetic transformation by combining the method developed by James et al. (1990) and Nehra et al. (1990) with a ballistic method. Physical damage to leaf disks was made by the microprojectile bombardment method.

In the above-cited methods the preparation of explants is based on a single-step procedure of preparing the whole amount of explants (James et al., 1990 and Nehra et al., 1990). A method is known, in which as explants use is made of whole laminas on which a maximum number of mechanical injuries is inflicted simultaneously (Trinh et al., 2000). Both of these methods increase the frequency of necrosis.

Humara et al, (1999) have shown that inflicting ultrasonic microtraumas on tender tissue of pine cotyledonary explants is accompanied by a lower frequency of necrosis. This method is applicable only for the embryonal tissues of germs or for any other cases when the regeneration proceeds from epithelial cells.

Publications are known, in which the method of genetic transformation is optimized for preventing necrotic reactions during the preparation of plant explants and their inoculation in an agrobacterial suspension.

Perl et al. (1996) tried to lower the frequency of necrosis by using antioxidants. Adding to the co-cultivation medium such components as DTT and PVPP made it possible to inhibit necrosis completely and succeed in producing fertile transgenic plants of grapes. However, the method is reproducible only on the plant material of one variety Superior Seedless.

Olhoft et al. (2001) have found that compounds with thiol groups, e.g., L-cysteine, are capable of increasing the frequency of transformation of *Glycine max* cells by agro-bacteria. The effect manifests itself only in the stage of co-cultivation of explants with agro-bacteria. The authors have also found that not only L-cysteine on adding to the co-cultivation medium can positively influence the process of transformation. A similar activity was displayed by such substances as glutathione, DTT, sodium thiosulfate, copper ions and iron chelates. The above-cited substances inhibit the activity of plant polyphenol oxidases and peroxidases, suppressing thereby the development of necrotic reactions caused by wounding or pathogens.

However, all the cited chemical components added to the nutrient medium not only influence the process of the interaction of bacteria with plant cells, but also produce a negative effect on the plant tissue of explants as such.

A combination approach for the elimination of necrosis is known (Hansen, U.S. Pat. No. 6,162,965). According to this method, in the stage of agrobacterial transformation chemical necrosis inhibitors are used, or an *agrobacterium* strain is selected which does not induce pronounced necrosis, or a genetic approach is used, in which, together with the gene of interest, the gene of specific necrosis-inhibiting factor is transferred into plant cells. Such factors have been known long since, but they have an extremely narrow species-specific activity. The author presents no data about the influence produced by the lowering of necrosis on lowering the overall level of somaclonal variations.

The known modifications of the methods of transformation influenced most often the frequency of the regeneration of transgenic shoots or the frequency of transgenic callus formation. None of the improved methods led to considerable lowering of somaclonal variations and morphological changes of transgenic plants with an enhanced resistance to phytopathogenic fungi. For example, in the expression of thaumatin in transgenic plants of cucumber (Szwacka et al., 2002) an enhancement of resistance to *Pseudoperonospora cubensis* was detected only in part of transgenic plants, and the recombinant protein-expression level did not correlate with the resistance level.

There is known a large number of plant proteins, which are to one extent of another toxic for phytopathogens and can be used in producing plants resistant to pathogenic fungi. This is, first of all, a vast group of RP-proteins (pathogenesis-related proteins), comprising five families PR-1-PR5 (Linthorst 1991). To these proteins there also belong antimicrobial peptides (thionines, defensines and lectins) and ribosome-inactivating proteins. The antifungal activity has been studied best of all in proteins belonging to two families PR-3 (glucanases) and PR-4 (chitinases). Both types of proteins belong in terms of the activity mechanism to hydrolyzing enzymes which destroy the structural components of the cytoderm of fungi.

The PR-5 family or thaumatin-like proteins in this aspect have been much less studied. They can display antifungal activity against a wide range of pathogenic fungi (Abad et al, 1996), e.g., such as *Alternaria solani, Aserrgillus flavus, Aspergillus parasitica, Bipolaris maydis, Bipolaris zeicola, Phytophthora fragariae, Verticillium alboatrum, Mycosphaerella fragariae, Diplocarponearlianas, Dendrophoma obscurans, Botrytis cinerea, Sphaerotheca humuli, Fusarium graminiarum, Fusarium oxysporum*, and others. There are no unambiguous communications about the antibacterial activity of thaumatin-like proteins in transgenic plants. It is known that, like the rest of the PR protein groups, they, apparently, perform protective function in plant cells. For instance, it is known that the expression of RS-5 (TL) proteins in plants is activated by attacks of pathogens, mechanical injuries, and also by such metabolites as salicylic acid and ABA (Stintzi et al. 1993). It is also known that such thaumatin-like protein from maize as zeamatin displays antifungal activity in vitro, but only in combination with the antibiotic Nikkomycin Z which inhibits the synthesis of chitin (Roberts et al. (1990). Hence, zeamatin behaves as a co-factor enhancing the action of the sublethal concentration of the antibiotic. Under the same conditions thaumatin also displays antifungal activity Dolgov et al. (1999) transferred thaumatin gene into plants of apple, carrot pear and strawberry. The authors have confirmed only the integration of the gene into the genome of the plants, but the protein expression in transgenic tissues was not analyzed.

Schestibratov et al (2001), by using the known method of genetic transformation (Jamers et al. 1990 and Nehra et al. 1990), have produced plants of garden strawberry with the gene of thaumatin. The recombinant protein expression was confirmed only in several transgenic lines.

None of the known methods provides the possibility for producing transgenic plants, say, of garden strawberry, with expression of thaumatin-like proteins and, particularly, of thaumatin, which display an enhanced resistance to phytopathogens and have a low level of somaclonal variations.

Known in the art is U.S. Pat. No. 5,856,154 (Ryals et al. 1999) for a method of protecting plants from pathogens, which provides the production of chimeric genes encoding PR-1 proteins and is based on using chemical agents for setting up conditions for the development of systemic acquired resistance (SAR). The authors select the types of genetic constructs with taking into account the use of facts relevant to the systemic acquired resistance of plants, which is yielded by plants in response to the influence of external factors.

Also known is a method of producing transgenic plants by introducing into a plant two genes producing an SAR effect (Baker et al., U.S. Patent Application 20020004944, 2002). Nevertheless, in these publications no data can be found which would support the fact that plants being transformed eventually show not only resistance, but also preserve all morphological characteristics.

DISCLOSURE OF THE INVENTION

One of the subjects of the invention is an improved method of agrobacterial transformation and regeneration of transgenic plants, which is characterized by low frequency of the necrosis of explants, enhanced frequency of transient expression, enhanced frequency of the regeneration of transgenic shoots, higher proportion of direct transformants, owing to the formation of acquired resistance to abiotic and biotic stresses in leaf disks, which eventually leads to lowering the frequency of somaclonal variations in the transgenic plant.

According to an improved method, the stages of the preparation, inoculation and co-cultivation of explants comprise the following steps:

i) a step of selecting one or more leaf segments for preparing explants; ii) a step of preparing leaf disks by separating a segment from each disk, followed by inoculating and co-cultivating leaf disks with agrobacteria; iii) a step of removing excess agrobacteria from leaf disks, separating a first lot of explants from the side of the first section, iv) a step of transferring explants onto the selection and regeneration medium; v) a step of preparing subsequent lots of explants in accordance with steps iii) and iv) till the last lot of explants from the selected leaf disks has been formed; wherein the preparation of each of the sub-sequent lots of explants is carried out after a time interval required for the transformation of plant cells and formation of acquired resistance to abiotic and biotic stresses in the leaf disks.

A next subject of the invention is a vector construct which contains genetic material coding for at least one peptide belonging to the group of target proteins and/or proteins responsible for enhancing the resistance to phytopathogens and/or for lowering necrosis.

Another aspect of the invention is that genetic material codes for the resistance of a transgenic plant to fungi selected from the group: *Phytophthora fragariae, Verticillium alboatrum, Mycospaerella fragariae, Diplocarpon earliana, Dendxrophoma obscurans, Botrytis cinerea, Sphaerotheca humuli*.

A further subject of the invention is a method of producing a transgenic plant which enters into the group of dicotgyledonous plants: apple, pear, garden strawberry, carrot, and tomatoes.

A still further subject of the invention is a method of producing a transgenic plant of garden strawberry, selected from the group of varieties: Selekta, Chambly, Chandler, Oka, Yamaska, L'Acadie, L'Authentique Orleans, Rosalyne, Roseberry, Saint-Pierre, Donna, Enzed Levin, Enzed Lincoln, Vilanova, Durval, Redcrest, Bountiful, Redgem, Pelican, Primtime, Mohawk, Latestar, Winoma, Feyerverk.

VARIANTS OF CARRYING OUT THE INVENTION

Figure 1A:
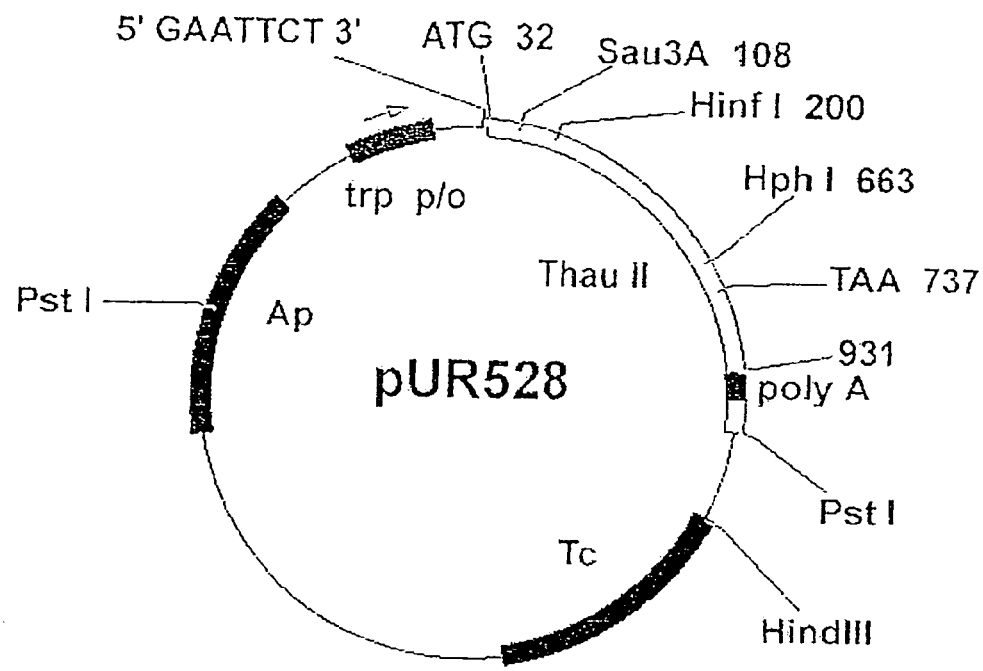
FIG. 1A shows diagrammatically plasmid pUR528.

An improved method of producing transgenic plants on the examples of garden strawberry and apple is based on the use of natural molecular mechanisms which are activated in plants in the process of the development of locally acquired resistance to abiotic and biotic stresses.

A method of producing transgenic plants with improved agronomic characteristics comprises the following steps.

In the first step the properties of a transgenic plant are selected and vector constructs for transferring the required genetic material into plant cells are produced.

In the second step the variety (genotype) is selected, stools are prepared for their subsequent sterilization and introducing into the culture in vitro, microclonal reproduction of the plant material is carried out, and rooted plants are prepared in vitro, which will serve as a source of leaf explants.

In the third step agrobacterial transformation is carried out with the use of constructed vector plasmids. For this purpose a bacterial suspension is prepared, leaves are collected and prepared, a stagewise inoculation and co-cultivation of the explants are carried out in accordance with the improved method.

In the next step selection of transgenic tissue, selection of transformants and elimination of agrobacteria are carried out and microclonal reproduction of the selected transformants is effected.

Transgenic plants having been produced, a molecular-genetic analysis of transgenic lines is carried out. For this purpose a total DNA is isolated from the tissue of the transgenic lines, PCR analysis of the heterologous DNA integration and histochemical analysis of the GUS-activity are carried out, along with Western-blotting for analyzing the expression of the target gene in the leaves and fruits of the transgenic lines.

In the final step, for selecting lines without somaclonal variations, biological testing is carried out: an analysis of resistance to phytopathogens; an organoleptic analysis of fruits; evaluation of the vegetative and generative activities of the transgenic plants in field conditions.

In the improved method of transformation the step of preparing, inoculating and co-cultivating explants with agrobacteria is carried out stagewise in the following manner.

Explants from the same leaves are cut not at the same time, before the inoculation, but in at least in more than two independent approaches with a periodicity of 1 to 5 days, more preferably in 3 days. The number of steps is selected in the range of from 2 to 5r, preferably from 3 to 4.

The explant width is selected within 0.5 to 10 mm, preferably within 1 to 3 mm. The ratio of the section length and the explant surface area is selected within 0.1 to 2 mm/mm$^2$, the more preferable value being 0.5 mm/mm$^2$.

For enhancing the transformation effectiveness, growth regulators and/or selective agents are comprised in the formulation of the selection and regeneration medium. Cytokinins and/or auxins are used as the growth regulators. For example, synthetic derivatives of phenylurea can be used as cytokinins, and IBA, IAA, PAA, 2,4-D and their conjugates with amino acids can be used as auxins. Nevertheless, for enhancing the acquired resistance to abiotic and biotic stresses, growth regulators can be excluded from the formulation of the co-cultivation medium. The selective agent is selected from the group comprising: neomycin, kanamycin, hygromycin, phosphinotricin. The combination, ratio and concentration of said components are selected depending on the genotype.

For instance, in the case of transformation of garden strawberry, the TDZ concentration is selected within the range of from 1 to 10 mg/ml. The optimal TDZ concentration is 5 mg/l. The TBA concentration is selected within the range of from 0 to 2 mg/l. The optimal TBA concentration is 0.3 mg/l. The kanamycin concentration is selected within the range of from 10 to 100 mg/l. The optimal kanamycin concentration is 50 mg/l.

For producing a transgenic plant with prescribed properties vector constructs are used, produced by the known method (Maniatis T. et al. 1982), which comprise a genetic material selected from the group consisting of a) a genetic material coding for at least one target protein; b) a genetic material coding for at least one protein which is instrumental in lowering necrosis at the step of transformation; c) a genetic material coding for at least one protein which enhances the plant resistance to phytopathogens and which is selected from the group: PR-1, PR-2, PR-3, PR-4, PR-5, d) a genetic material whose coding sequence may consist of at least two sequences related to sub-items a) and b), ort a) and c), or b) and c), or a), b), c).

For producing a plant with enhanced resistance to pathogens, the genetic construct comprises genes coding for the resistance to fungi e selected from the group consisting of *Phytophthora fragariae, Verticillium alboatrum, Myucosphaerella fragariae, Diplocarpon earliana, Derndrophoma obscurans, Botrytis cinerea, Sphaerotheca humuli.*

For instance, for producing a transgenic plant of garden strawberry with enhanced resistance to *Botrytis cinerea*, vector construct pBITau35 is used, which comprises the thaumatin II gene (Schestibratov et al. 2002).

As a result of genetic transformation, plants are produced, which contain genetic material coding for at least one protein entering into the group of target proteins and/or proteins responsible for the enhancement of resistance to phytopathogens and/or for lowering of necrosis.

As the target product use can be made of proteins, which: a) enhance the nutritive value, b) improve the taste, c) impart resistance to herbicides, d) are of pharmaceutical importance.

The improved method of genetic transformation can be used for monocotyledonous and dicotyledonous plants.

For producing transgenic plants with enhanced nutritive value, improved taste, and enhanced resistance to phytopathogens dicotyledonous plants can be selected.

For example, for the transformation plants are used, selected from the group: apple, pear, garden strawberry, carrot and tomatoes.

Transgenic plants of garden strawberry can be produced, selected from the group of varieties: Selekta, Chambly, Chandler, Oka, Yamaska, L'Acadie, L'Authentique Orleans, Rosalyne, Roseberry, Saint-Pierre, Donna, Enzed Levin, Enzed Lincoln, Vilanova, Durval, Redcrest, Bountiful, Redgem, Pelican, Primtime, Mohawk, Latestar, Winoma, Feyerverk.

Examples in a detailed description are given for garden strawberry of Feyerverk and Selekta varieties and for apple of Melba variety.

For practical application transgenic plant components can be used: transgenic cells, organs (leaves, stalks, roots, flowers), whole plants, seeds and fruits.

Figure 3:
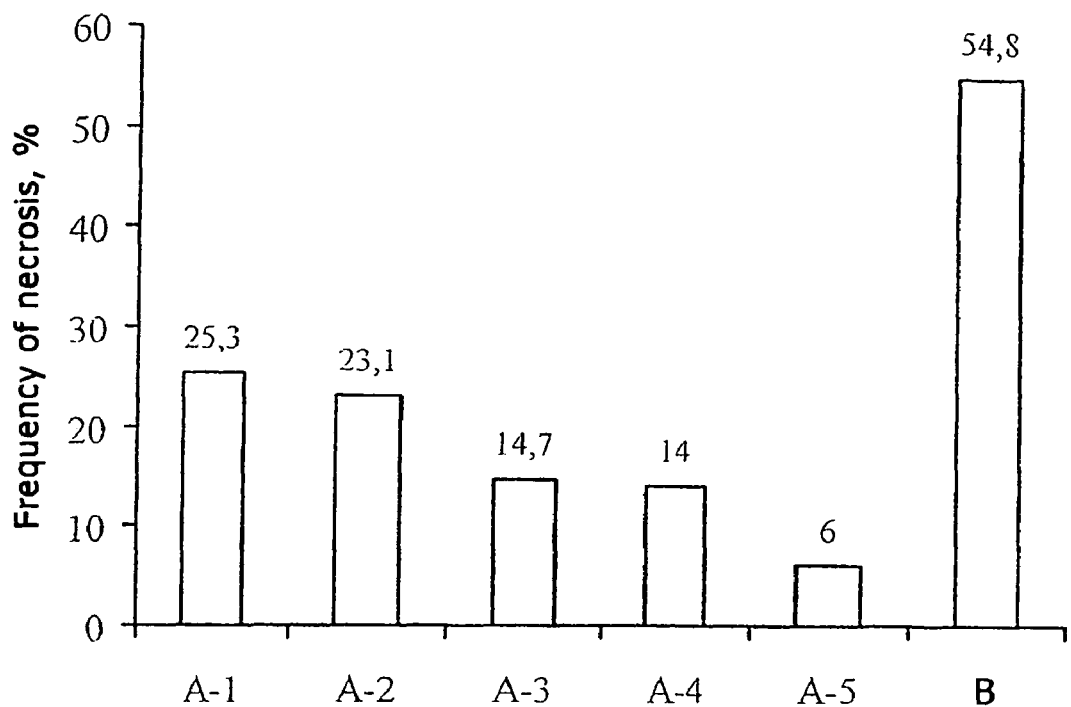
FIG. 3 illustrates the influence of stagewise co-cultivation with *Agrobacterium thumefaciens* on the frequency of necrosis in the tissues of explants of garden strawberry of the Feyerverk variety.
Figure 4:
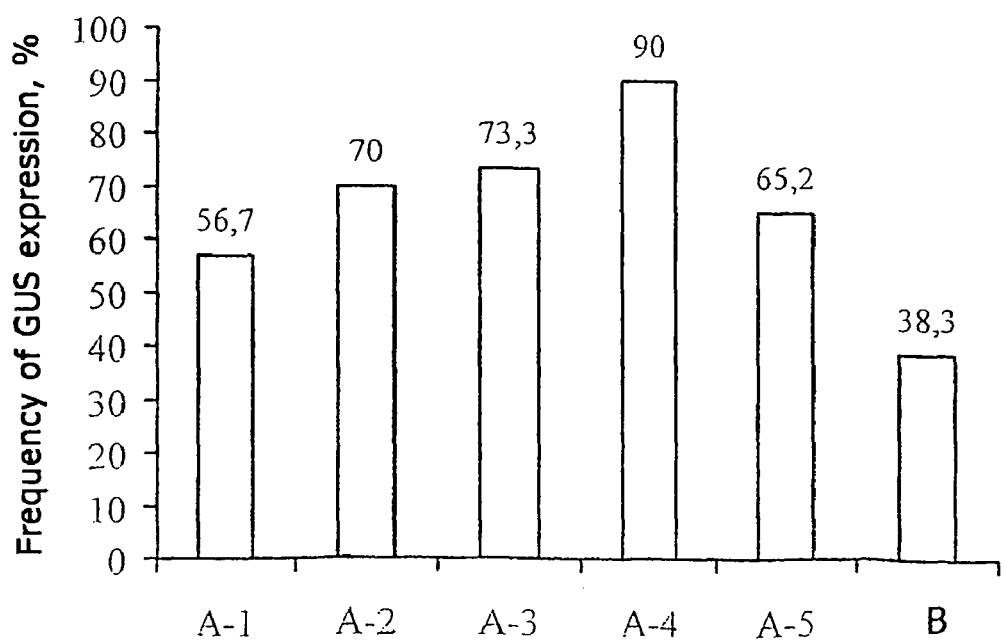
FIG. 4 illustrates the influence of stagewise co-cultivation with *Agrobacterium thumefaciens* on the transient GUS-expression in the tissues of explants of garden strawberry of the Feyerverk variety.
Figure 5:
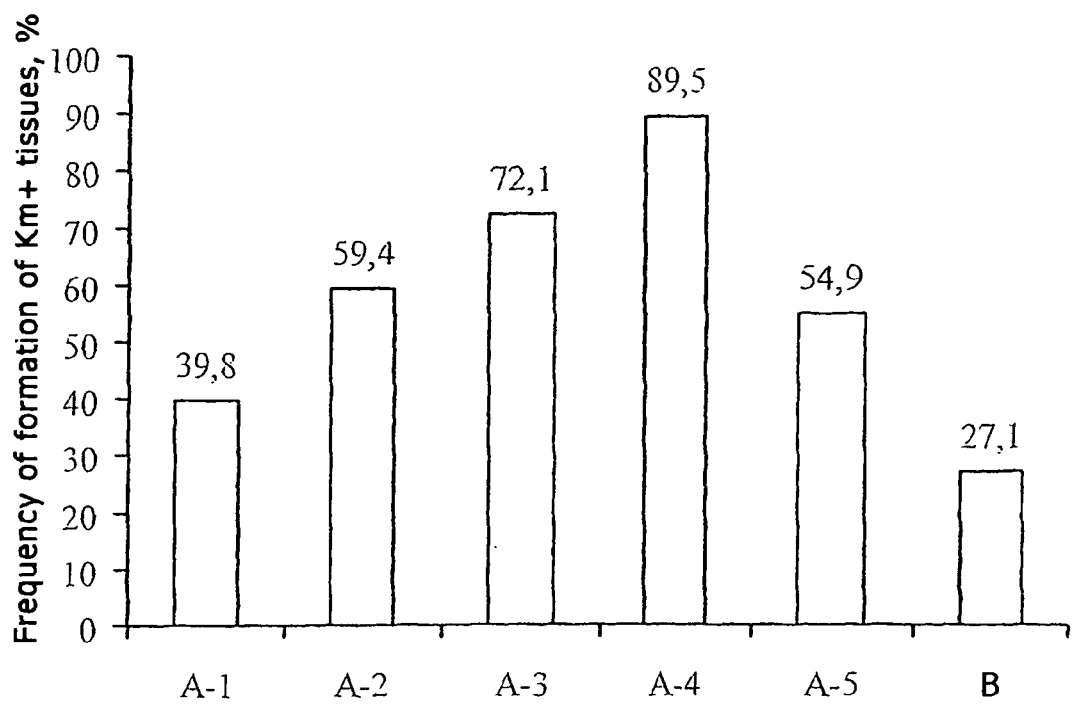
FIG. 5 illustrates the influence of stagewise co-cultivation on the frequent cy of formation of tissues resistant to kanamycin (Km+) on the starting explants of garden strawberry of the Feyerverk variety.
Figure 6:
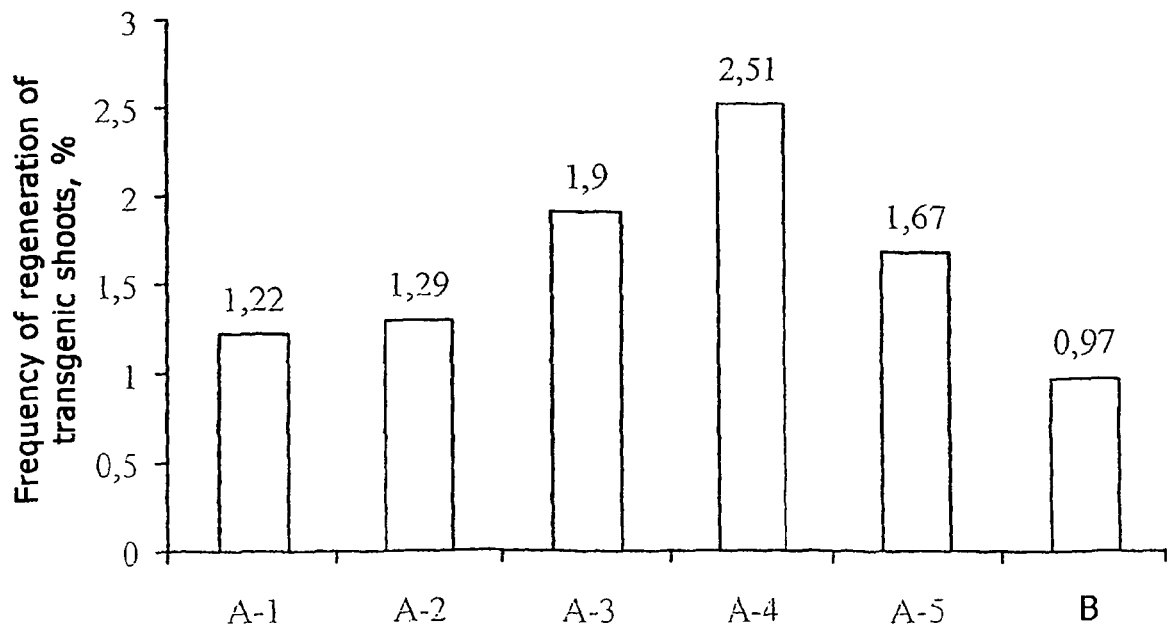
FIG. 6 illustrates the influence of stagewise co-cultivation with *Agrobacterium thumefaciens* on the frequency of regeneration of transgenic shoots of garden strawberry of the Feyerverk variety.

Modifications introduced into the method of agrobacterial transfer make it possible to make the following improvements in the parameters of the method as such and in the characteristics of transgenic plants. The method makes it possible: to lower the frequency of development of necrotic reactions on the explants being transformed (FIG. 3); to raise the frequency of transient expression of the genes being introduced (FIG. 4); to raise the frequency of formation of new transgenic tissues on the initial explants (FIG. 5); to increase the ratios of direct regenerants to the number of regenerants produced via the callus stage (Table 6); raise the frequency of regeneration of transgenic shoots (FIG. 6); finally, to increase the proportion of plants without somaclonal variations among transgenic lines (Table 11).

Experimental Protocols

These experimental protocols relate to the methods, conditions and components of media for the procedure of producing transgenic plants with an enhanced resistance to phytopathogens and improved taste characteristics on the example of garden strawberry. These protocols include but do not limit changes in the concentration parameters, time-related conditions and other changes which are obvious from the general state of the art and come into the scope of protection of the present invention.

A. Materials and Methods used in Producing a Transgenic Plant Constructing a Vector Plasmid for Transferring into Plant Cells Preprothaumatin II Sequence Encoding Thaumatin II Protein.

The thaumatin II gene encodes the super-sweet protein which is encountered in nature in fruits of *Thaumatococcus dantelli* from which it was isolated and characterized. The sequence comprises preprothaumatin II—a precursor of mature thaumatin, which contains a native signal peptide. Cloning of thaumatin cDNA is described in Edens et al, 1982. The use for the expression in cells of *E. coli* is shown by Verrips et al (U.S. Pat. No. 4,891,316).

The vector plasmid for transferring into plant cells of the preprothaumatin II sequence, encoding thaumatin II protein, was constructed with the use of well-known molecular cloning methods (Sambrook et al., 1989).

Figure 1B:
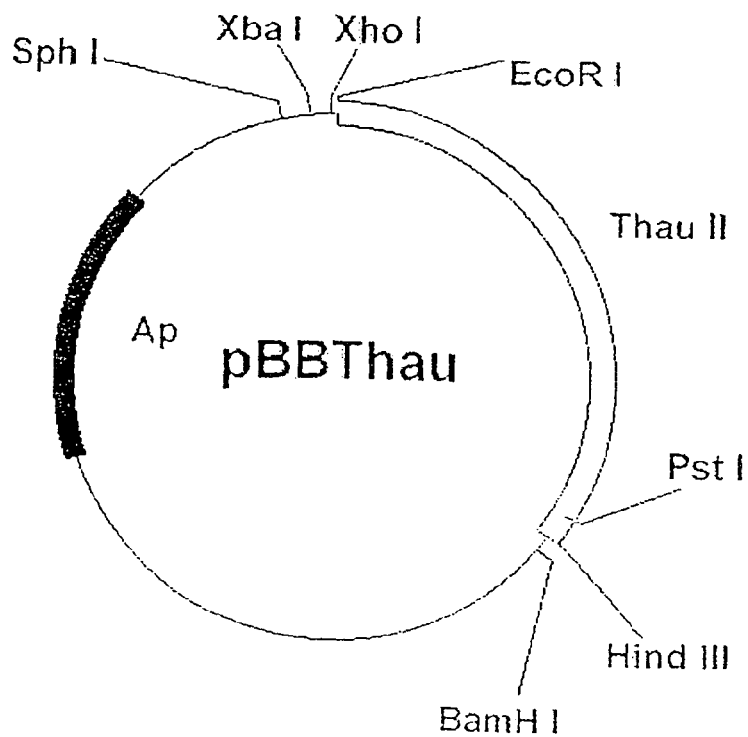
FIG. 1B shows diagrammatically plasmid pBBThau.
Figure 1C:
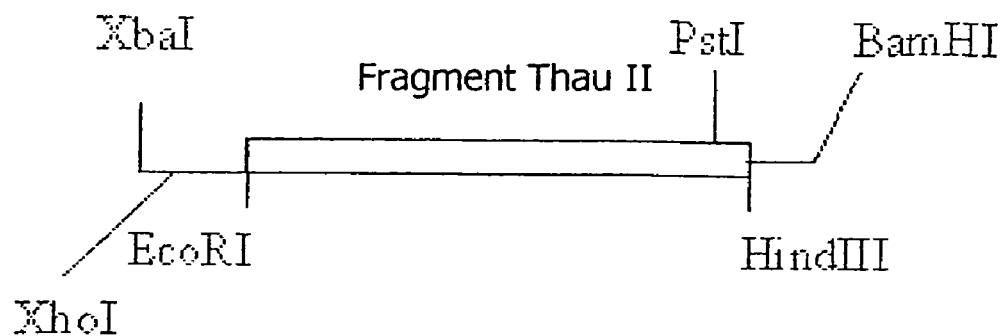
FIG. 1C shows a restriction fragment XbaI-BamHI from plasmid pBBThau carrying preprothaumatin II.
Figure 2:
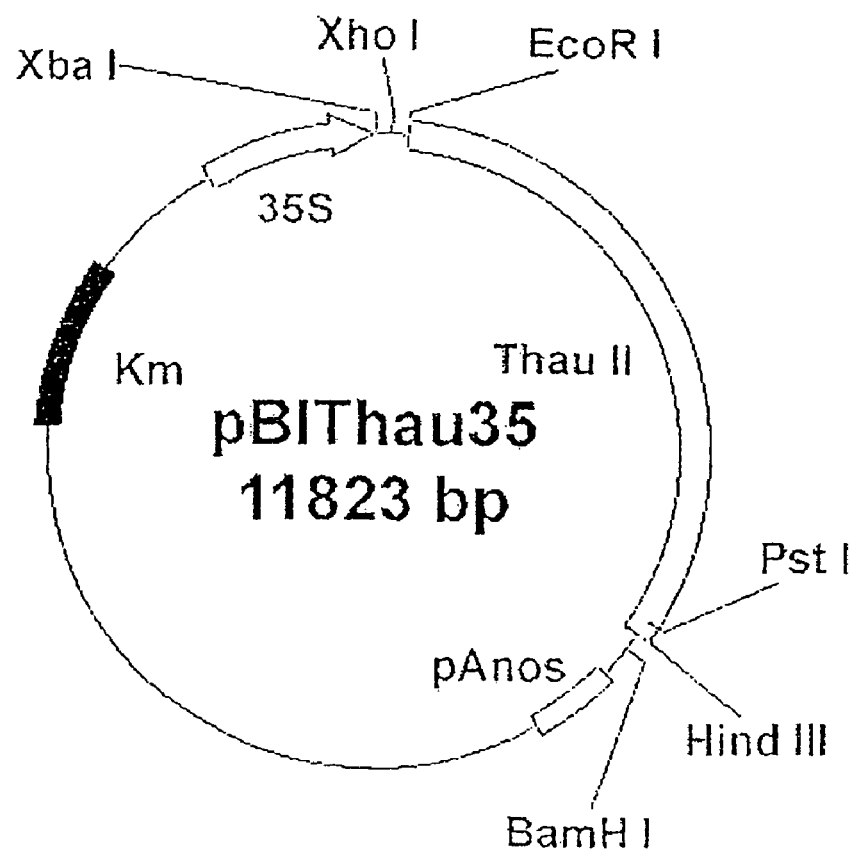
FIG. 2 shows diagrammatically binary vector pBITau35. LB and RB are left-hand and right-hand terminal repeats of T-DNA; Panos is a terminator from the gene of nopalin synthetase; pNOS is a promoter from the gene of nopalin synthetase; p35S is a promoter of 35S RNA of cauliflower mosaic virus; nptII is a gene of the plant selective marker of neomycin phosphotransferase; thauII is preprothaumatin II sequence coding for super-sweet protein thaumatin II.

Plasmid pBI121 (Clontech Co.) was taken as a basis for transferring the given gene into plant cells. The sequence of the gene gus in this plasmid was changed by the preprothaumatin II fragment from plasmid pUR528 (Unilever Research Laboratorium, The Netherlands; Erdens et al., 1982; (FIG. 1A) the preprothaumatinII fragment from the plasmid pUR528 was excised with respect to EcoRI and HindIII sites. The intermediate vector pBB (selective marker Ap) carrying the polylinker SphI-XbaI-XhoI-EcoRI-SmaI-Ava-BamHI-XbaI-SDauI-PstI-HindIII-BamHI-BstXI-NciI was incubated with EcoRI and HindIII restrictases. The preprothaumatin II fragment with sticky ends along the EcoRI and HindIII sites was ligated into linearized pBB vector along the same sites. The obtained pBBThau plasmid (FIG. 1B) was incubated with the XbaI and BamHI, with as view to cutting out again the preprothaumatin II fragment, but this time with new sticky ends (FIG. 1C). Binary vector pBI121 was first incubated with SmaI and SacI restrictases, then the linearized form of the plasmid was ligated along blunt ends, then the preparation was incubated with the XbaI and BamHI restrictases. The XBaI-BamHI fragment of the preprothaumatin II sequence, preliminarily excised from the pBBThau vector, was ligated into the linearized pBI121 vector. The pBIThau vector is shown diagrammatically in FIG. 2.

Media for Cultivating Garden Strawberry in Vitro and Carrying out Genetic Transformation. Media for the multiplication (M) elongation and rooting (ER), co-cultivation (CC) and regeneration of transformants (RT) are prepared in accordance with the data presented in Table 1. In all the media pH is adjusted to 5.5.

TABLE 1

Media for cultivation of garden strawberry in vitro and carrying out genetic transformation

| Components | Concentration | | | |
| --- | --- | --- | --- | --- |
| | M medium | ER medium | CC medium | RT medium |
| Potassium nitrate | 316 mg/l | 316 mg/l | 2900 mg/l | 2900 mg/l |
| Ammonium nitrate | 400 mg/l | — | 1650 mg/l | 1650 mg/l |
| Monosubstituted potassium phosphate | 170 mg/l | 170 mg/l | 170 mg/l | 170 mg/l |
| Calcium nitrate × 4H$_2$O | 1133 mg/l | 1133 mg/l | — | — |
| Calcium chloride | — | — | 332.2 mg/l | 332.2 mg/l |
| Magnesium sulfate × 7H$_2$O | 369 mg/l | 369 mg/l | 180.7 mg/l | 180.7 mg/l |
| MS microsalts | 32.83 mg/l | 32.83 mg/l | 32.83 mg/l | 32.83 mg/l |

TABLE 1-continued

Media for cultivation of garden strawberry in vitro and carrying out genetic transformation

| Components | Concentration | | | |
|---|---|---|---|---|
| | M medium | ER medium | CC medium | RT medium |
| Iron sulfate × 7H$_2$O | 27.8 mg/l | 27.8 mg/l | 27.8 mg/l | 27.8 mg/l |
| Na$_2$EDTA × 2H$_2$O | 37.26 mg/l | 37.26 mg/l | 37.26 mg/l | 37.26 mg/l |
| Sucrose | 30 g/l | 20 g/l | 30 g/l | 30 g/l |
| MS vitamins | 3.5 mg/l | 3.5 mg/l | 3.5 mg/l | 3.5 mg/l |
| Myo-inositol | 100 mg/l | 100 mg/l | 100 mg/l | 100 mg/l |
| Agar | 8 g/l | 8 g/l | 8 g/l | 8 g/l |
| BAP | 1 mg/l | — | — | 4 mg/l |
| TDZ | — | — | — | 1 mg/l |
| IBA | — | — | — | 0.3 mg/l |

Selection of Variety and Preparation of Stock Plants

In the experiments on genetic transformation of strawberry, in vitro material of the following plants was used: a) of the Feyerverk variety (Zubov A. A., VNII Genetiki I Selektsii Plodovykh Rastenij im. I. V. Michurina, Michurinsk) and b) of the Selekta variety (Evans E., South Africa, 1973, PI 551873).

Garden strawberry was introduced into the culture in vitro by sterilizing young apical buds from the tendrils of open ground plants. For this purpose tip buds were cut off with a small shoot fragment no bigger than 5-10 mm, then cleared from surface leaflets, soaked in an aqueous solution of Tween 20 for 1 hour, after that washed under running water for 2 hours. For sterilizing, washed explants were kept for 1-5 minutes, depending on their size and age, in a 2% solution of sodium hypochlorite. After that the explants were washed thrice in 100 ml of sterile distilled water.

The surface-sterilized shoots were planted separately into test tubes with 10 ml of the medium for multiplication (M medium, see Table 1). The main components of this medium correspond to the MS medium (Murashige et al. 1962) improved according to Boxus (1974), only with two modifications: first, glucose in the concentration of 22 g/l was replaced by 30 g/l of sucrose; second, for stimulating the multiplication, the medium was complemented with 5 Mm of ammonium nitrate. After keeping for one month in the culture, whole uninfected explants with newly formed shoots were replanted onto the elongation and rooting medium (ER medium, se Table 1), which differs from the M medium by the absence of growth regulators, additional ammonium nitrate and lowered sucrose concentration (2%). On an average in 4-6 weeks the grown up shoots are separated from one another and planted onto a fresh medium having the same formulation, to stimulate rooting. The rooted plants were used as the source of leaf disks in subsequent regeneration and transformation experiments. Such plants are cultivated on the ER medium for 7-8 months, with replanting every month onto a fresh medium. For growing sterile material of strawberry, special 250 ml screw-cap cultivating jars (Hort-Mic, Finland) were used.

Preparation of Bacterial Suspension

For the genetic transformation with binary strains pBI121 and pBIThau35, super-virulent strain *Agrobacterium thumefaciens* CBE21 (Revenkova et al. 1994) was used, constructed on the basis of wild strain *A. thumefaciens* with Ti-plasmid pTiBo542.

Bacterial suspensions of the strains CBE21/pBITThau35 and CBE21/pBI121 for the inoculation of the explants were built up overnight in 50 ml of the LB medium (Table 2) at 28° C. Before the inoculation, the cell suspension was centrifugated at 5000 rpm for 5 minutes. The precipitate was washed twice with 50 ml of liquid MS medium to remove residues of the LB medium. The washed cell residue was re-suspended in liquid MS medium, then the suspension density was brought to OII600 equal to 1.

TABLE 2

LB medium for cultivation of agrobacteria

| Component | Concentration |
|---|---|
| Sodium chloride | 10 g/l |
| Bacto Trypton | 10 g/l |
| Yeast extract | 5 g/l |
| pH | 7.5 |

Collecting and Preparing Leaves

Young fully unfolded trifoliums were cut off the stools prepared by the above-described method directly before setting up the genetic transformation. The size of a separate leaf disk in each trifolium varied within 10-15 mm (in a direction of the central vein). To reduce shrinkage of the leaves in the course of subsequent operations, they are kept in closed Petri dishes with a small quantity (20 ml) of liquid MS medium. Leaves are cut off the plants not oftener than twice a month. The stools before and after collecting the leaves are cultivated under the same conditions of a 16-hours' daylight period.

Preparation, Inoculation and Co-Cultivation of Explants

The cut-off trifoliums are separated into individual leaf disks which, in their turn, are cut with a scalpel into explants by various methods.

Improved Method of Preparing Inoculating and Co-Cultivating Explants

In the proposed method leaf disks are cut with a scalpel on a Petri dish in the presence of a small quantity of liquid MS medium From 10-15 mm leaf disk (in a direction of the central vein) a narrow strip having a width not exceeding 2 mm is cut off and then discarded The remaining larger part of the leaf disk (explant A-5) is used later for the inoculation.

In the first step explants A-5 immediately after cutting them off are transferred carefully with pincers into the bacterial suspension and soaked there for 30 minutes, Then explants A-5 are transferred into clean Petri dishes with paper filters and dried a little for 5 minutes to remove excess bacteria. After that these explants are placed into Petri dishes with the CC medium, the surface of which is covered with a paper filter. The dishes are wrapped with parafilm and incubated in a temperature-regulated chamber in darkness at a temperature of 25-28° C. for 3 days.

Then explants A-5 are transferred into a beaker with liquid MS medium, and stirred intensively for 3-5 minutes to remove excess bacteria. The washed explants are transferred into Petri dishes with a small quantity of liquid MS medium. From each of the explants A-2 a narrow strip having a width of about 2 mm is cut off with a scalpel from the side of the first section, thus forming first-stage explants. Explants A-1 are collected into as beaker with liquid MS medium. After that explants A-1 are placed into Petri dishes onto the surface of RT medium to which 500 mg/l of cefotaxime are added, and intensively stirred to remove agrobacteria residues. After that explants A-1 are placed into Petri dishes onto the surface of RT medium with the rear side facing the medium. The dishes are wrapped into parafilm and incubated in a temperature-regulated chamber in darkness at a temperature of 23-25° C. Explants A-5 are returned again onto the same CC medium, where the paper filter was preliminarily changed. The dishes are wrapped into parafilm and incubated in a temperature-regulated chamber in darkness at a temperature of 25-28° C. for the next 3 days.

In the second step explants A-5 are transferred into a beaker with liquid MS medium, intensively stirred for 3-5 minutes to remove excess bacteria. The washed explants are transferred into Petri dishes with a small quantity of liquid MS medium. A next strip having a width of 1 to 2 mm is cut off with a scalpel from explants A-5 from the side of the first section, second-stage explants being thus formed. Explants A-2 are collected into a beaker with liquid MS medium to which 500 mg/l of cefotaxime are added, and intensively stirred to remove agrobacteria residues. After that explants A-2 are placed into Petri dishes onto the RT medium with the rear side facing the medium The dishes are wrapped into parafilm and incubated in a temperature-regulated chamber in darkness at a temperature of 23-25° C. Explants A-5 are returned again onto the same CC medium, where the paper filter was preliminarily changed. The dishes are wrapped into parafilm and incubated in a temperature-regulated chamber in darkness at a temperature of 25-28° C. for the next 3 days.

In the third step and in the fourth step from explants A-5 third-stage explants A-3 and fourth-stage explants A-4 are formed in accordance with the procedure described for the second step.

In the fifth step the last explant A-5 is treated, which is transferred into a beaker with liquid MS medium, intensively stirred for 3-5 minutes to remove excess bacteria. After that the explant is washed with liquid MS medium to which 500 mg/l of cefotaxime are added to remove agrobacteria residues. After that explants A-2 are placed into Petri dishes onto the RT medium with the rear side facing the medium. The dishes are wrapped into parafilm and incubated in a temperature-regulated chamber in darkness at a temperature of 23-25° C.

The known method of preparing, inoculating and co-cultivating explants (James et al., 1990) is used as control.

Selection of Transgenic Tissue, Selection of Transformants and Elimination of Agrobacteria After the inoculation and co-cultivation with agrobacteria, explants are placed into Petri dishes onto the surface of RT medium complemented with 600 mg/l of casein hydrolyzate, 500 mg/l of cefotaxime and 50 mg/l of kanamycin. The dishes are wrapped into parafilm, and incubated in a temperature-regulated in darkness at a temperature of 25-28° C. Cefotaxime is used for the elimination of agrobacteria residues on the explants. Its concentration is varied during the passages with every monthly passage, the level is lowered by 100 mg/l from the initial 500 mg/l to the final 0 mg/l. Kanamycin plays the role of selective agent, because in vector constructs the neomycin nptII transferase gene is used as the selective marker. The working concentration of kanamycin, sufficient for inhibiting the growth of the non-transgenic tissue of garden strawberry is 50 mg/l. However, for stimulating the regeneration of adventive shoots, the concentration of kanamycin in the medium is reduced by one half after separating callus pieces from the initial tissue and transferring them onto a fresh medium. Separating transgenic callus from the necrotic tissue of the explants is the crucial moment of the process of selection and regeneration of the transformants. The effectiveness of the transformation without this procedure lowers markedly.

The regeneration of the transformants of strawberry can proceed in two ways: directly from the cells of the explants and/or via the intermediate callus stage. In the first case transformants appear from the first through the second month of selection. Regeneration via the callus stage is appreciably extended in time, transformants may appear from the third through the sixth month of cultivation on the selective medium.

Multiplication of Transformants

The shoots that have regenerated are separated from the initial tissue of the explants and transferred for the multiplication onto the M medium (Table 1), complemented with 0.1 mg/l of TDZ and 2.5 mg/l of kanamycin. After a one month's passage, the multiplied shoots are transferred in whole clusters onto the ER medium for stimulating the elongation of the shoots. After 4-5 weeks the grown up shoots are separated one from the other and planted separately on a fresh medium of the same formulation to stimulate rooting. Rooting proceeds during 4-6 weeks. The rooted plants are used later on for the adaptation to green-house conditions and subsequent molecular-genetic analysis and biological testing.

B. Materials and Methods for Analyzing Transgenic Plant Properties

Isolation of Total Plant DNA of Garden Strawberry

For the extraction of genomic DNA use was made of both in vitro and in vivo plant material. From the in vitro conditions for the trituration in liquid nitrogen whole shoots cultivated on the medium for the multiplication were taken. From green-house plants young, yet unfolded leaflets were cut off In both cases the age and physiological condition of the plant tissue strongly influenced the purity the purity of the preparations. For sterile material the optimal age of the shoots was 3-4 weeks; for green-house material the age of the leaflets was not more than 5-6 days. Isolation was carried out according to the protocol modified by us. The procedure of Rogers et al. (1994) with the use of $2^x$ STAV buffer was adopted as the basis.

In contradistinction to the protocol according to Rogers et al. (1994), homogenized tissue is re-suspended in 1 ml of a washing buffer: 100 mM of potassium acetate, pH 4.5, 20 mM EDTA, 1% PVP, 1% 2-ME. The resulting suspension is centrifuged for 5 minutes at 4.500 rpm. The supernatant liquid is removed. The precipitate is again resuspended in 600 µl of an extraction STAV buffer having the following composition: 100 mM of tris-HCl, pH 8, 2.5 M NaCl, 20 mM of EDTA, 2% STAV, 40 mM of 2-ME.

PCR Analysis of Transgenic Lines

The lines prepared with the aid of any of the employed vector constructs are analyzed with two pairs of primers: for the insertion of selective marker (nptII) and for the insertion of sense gene (thauII) or reporter gene (uidA).

The PCR analysis of the integration of different heterologous sequences into the genome of garden strawberry is carried out in a reaction medium which contains: 67 mM of Tris-HCl, pH 9.0, 16 mM of $(NH_4)_2SO_4$, 2 mM of $MgCl_2$, 0.01% gelatin, 200 µM of each dNTP. The concentration of the primers and of the polymerase and the temperature conditions are selected for each particular case.

For the amplification of the of the gene nptII fragment, primers to 0.6 mM final concentration and 0.05 U/µl of Taq polymerase are introduced into the reaction mixture. Amplification conditions: 5 minutes of denaturation at 94° C. (hot start), 30 seconds of denaturation at 93° C., annealing—45 seconds at 62° C., elongation—45 seconds at 62° C., 30 amplification cycles. The expected size of the fragment being amplified is 742 nucleotides.

The insertion of thauII was determined under conditions for the most part similar with those for nptII, only the concentration of the primers was 0.9 µM each, 0.1 U/µl of the polymerase, and the temperature conditions were changed as follows: hot start, 2 min 94° C.; denaturation, 30 s 93° C.; annealing, 40 s 63° C.; elongation, 35 s 72° C.; 35 amplification cycles. The expected size of the fragment being amplified is 878 nucleotides (Schestibratov et al., 2002).

Histochemical Analysis of GUS Activity

Histochemical determination of GUS activity was carried out by the method of Jefferson (1987). The histochemical determination of the GUS activity was carried out with the use of 5-bromo-4-chloro-3-indolyl glucoronide (X-GLUC, Duchefa). For the determination, plant tissue was placed into a buffer: 50 mM of $NaPO_4$, pH 7.0, 10 mM of $Na_2EDTA$, 0.12% Triton X-100 containing 1 mg/l of X-GLUC, incubated for 6 hours at 37° C. After that the tissue was washed several times with 50% ethanol, and stained tissues were stored at 4° C. in 70% ethanol.

Organoleptic Analysis of Garden Strawberry Fruits

Fruits for the organoleptic analysis were gathered from transgenic plants cultivated in field conditions on the certified site for testing transgenic cultures on the territory of the VNIISPK quarantine garden (at Orel). Fruits of the first yields of the first and second years of cultivation were tasted. Fruits of 12 independent transgenic lines and control lines were evaluated according to their taste qualities, first of all, by sweetness. The sweetness of the fruit pulp was evaluated in terms of a five-point system, proceeding from the Feyerverk variety characteristic, according to which the taste of middle-ripening fruits of the first yield does not exceed 3.8 to 4.0 points.

In connection with the specific properties of thaumatin which is responsible for long-term aftertaste, the organoleptic analysis was carried out pairwise. For this purpose fruits of two different plants were taken and pairs were formed: a) line with thaumatin expression—line without thaumatin expression, b) line with thaumatin expression—non-transgenic plant.

Combinations were made up arbitrarily, with taking into account only the data about the presence or absence of protein. After tasting each sample, tasters gargled their oral cavity with distilled water. In order to rule out or at least decrease the effect of differences in ripeness on the correctness of the analysis, fruits of the same size and color were chosen for tasting. The weight of the fruits varied from 10 to 15 grams. One taster for comparison for each line was given four sections, each from different fruits. The tasters allotted independent points, the arithmetic mean serving as the taste rating for the given specimen.

Analysis of the Influence of Thaumatin II Expression on Antifungal Resistance of Garden Strawberry to *Botrytis cinerea*

The culture of the phytopathogen *Botrytis cinerea* is isolated from infected fruits of garden strawberry of the Feyerverk variety. Repeated re-inoculation of uninfected fruits and leaves confirmed the virulence of the isolated and purified pathogen. The culture of the pathogen under in vitro conditions was maintained on potato medium PDA, in darkness at 28° C. For preparing this medium, a decoction of pealed potato in tap water was used (200 g of potato per liter of water cooked for 30 minutes after boil). 10 g/l of glucose and 20 g/l of bacteriological agar were added to the decoction. The medium was auto-claved under pressure of 1 atm and at 120° C. for 20 minutes. After autoclaving, casein hydrolyzate was added to the medium to the final concentration of 300 mg/l.

For preparing a suspension of spores, a 7-8 days' culture of the fungus was used. After passage on a fresh medium, during a week new mycelium develops from the spores, and sporogenesis starts on the $7^{th}$ to $8^{th}$ day. Spores were gathered with a sterile spatula which was each time rinsed in a solution of 25 mM sodium acetate (pH 5.2) with 5% glucose and a detergent (2 drops of Triton X100 per 20 ml). The density of the suspension for all the bioassays was brought to $2-3\times10^6$ spore/ml. Density counts were carried out in a Goryaev chamber.

Transgenic plants produced with the aid of the vector construct pBIThau35 were analyzed for resistance to the phytopathogen *Botrytis cinerea* in accordance with the method described in Peng et al. 1991 with additional improvements which are described below. Material for the bioassay was taken from green-house plants not older than 4-6 months. Before the inoculation, leaves were slightly died at room temperature. Inoculation was carried out by wetting leaves with the suspension of spores for 1-2 minutes. The inoculated leaves were placed into Petri dishes onto moist filters and incubated during 24 hours in darkness at 28° C. Then the leaves were sterilized in a 0.5% solution of sodium hypochlorite for 2 minutes. The sterilizing agent was washed away thrice with 100 ml of sterile distilled water. Leaf disks were cut from the leaves with a cork drill of 7 mm in diameter. 10 disks were made from each trifolium. In contradistinction to the known method, the disks were placed onto moistened filters rather than onto an agarized medium with additions of paraquate and chloramphenicol.

The experimental and control materials were compared pairwise within one Petri dish to avoid the influence of humidity fluctuations of the filters and air inside the chamber. The already cut and placed leaf disks were incubated under the same conditions as the whole leaves. On the tenth day the development of the infection was assessed on the basis of three criteria: 1) the degree of development of the surfaced mycelium; 2) the area of the necrotic lesion of the leaf disks; 3) the degree of sporogenesis. The first and third criteria were evaluated in points from 0 to 5. The degree of necrosis was evaluated in the percentage of the area of the affected part of the disk.

Field Tests of Transgenic Plants of Garden Strawberry with the Gene of Super-sweet Protein Thaumatin II A large part of the transgenic plants produced with the help of the vector pBIThau35 was transferred to the VNIISPK quarantine garden (at Orel) for planting in open ground and carrying out field tests.

When planting the transgenic lines and control plants, randomization was carried out. The plants intended for planting, (5 to 10 for a separate line) were distributed into three groups, each of which was planted in different locations of a certified plot.

Four new rosettes from formed tendrils were rooted from each stool plant. For the planting not to be crowded, the rest of the tendrils were regularly removed. Before the onset of flowering, the plot was covered with a protecting material for preventing the propagation of the pollen of the transgenic plants. An individual cover of about 60 cm in height was erected above each of the three rows. After gathering the first yield of the fruits, the vegetative and productive activities of the planted plants were evaluated. The number of rosettes in a shrub, the number of peduncles and an average height of the shrub were counted. One month after the gathering of the second yield, the fruits of the first and second yields were used for analyzing the thaumatin expression by the method of Western blotting, and also for organoleptic evaluation of the effect produced by heterologous protein on the taste of the fruits.

EXAMPLES

Example 1

The Influence of Stagewise Co-Cultivation with Agrobacterium thumefaciens on the Frequency of Necrosis in the Tissues of Explants of Garden Strawberry of the Feyerverk Variety The frequency of necrosis of the explants was evaluated visually after 15 days of cultivation on the selective medium. The plant material transformed by following the standard and improved methods was compared. The obtained data suggest that the improvement of the inoculation and co-cultivation stages tells positively on the survival of the explants and on preventing the development of necrotic reactions in the places of wounding. The data on the average frequency of the necrosis of the explants transformed according to the improved method (A), 16.6%, and according to the known method (B), 54.8%, show that the necrosis of the tissues was lowered almost by the factor of 3.5. The data are presented in FIG. 3.

Example 2

The Influence of Stagewise Co-Cultivation with Agrobacterium thumefaciens on Transient GUS Expression in the Tissues of Explants of Garden Strawberry of the Feyerverk Variety In the genetic transformation with the use of Agrobacterium thumefaciens, T-DNA with the required heterologous sequences is transferred into plant cells predominantly in the wounded sites, where direct contact of the bacteria with the injured cells is ensured. For evaluating the effectiveness of the proposed method, histochemical analysis of the GUS activity in the tissues of the explants was carried out on completion of the co-cultivation period. Such analysis makes it possible the frequency of the transfer and expression of the recombinant genes in the T-DNA composition from the bacteria into the plant cells. The plant material for the analysis is selected on expiration of the 3-days' period of co-cultivation, immediately after washing-off the explants from the bacteria. Histochemical staining of the explants is carried out for 7 hours at 37° C. in an X-Gluc solution for the histochemical analysis of the GUS activity. The results of the analysis are presented in FIG. 4.

Example 3

The Influence of Stagewise Co-Cultivation with Agrobacterium thumerfaciens on the Frequency of Formation of Kanamycin-Resistant Tissues (Km+) on the Initial Explants of Garden Strawberry of the Feyerverk Variety In subsequent co-cultivation (after their stagewise co-cultivation with agrobacteria) on the RT medium complemented with 500 mg/l of cefotaxime and 50 mg/l of kanamycin, during first two monthly passages on the explants there takes place formation of direct transformants and non-organized callus groups. Km+ tissues (regenerants and callus groups) are formed predominantly on the sites of wounding.

By the end of the second passage the proportion of the explants on which transgenic tissue was formed, was calculated. From stage A-1 through stage A-4 a stable growth of the frequency of formation of Km+ tissues is observed. Apparently, this is associated, in the first place, with a decrease in the intensity of necrotic reactions in response to wounding and to the subsequent co-cultivation with agrobacteria, in the second place, with possible increase of the morphogenetic potential. In stage A-4 maximum proportion of the explants which have formed transgenic tissues was registered (89.5%, see FIG. 5). A reduction of the proportion of the explants which have formed transgenic tissues in group A-5 (54.9%) is explained by that in the fifth stage the number of plant cells competent for the genetic transformation already lowers. In control group B transgenic tissue formed on 27.1% of the explants, this being in good correlation with the high frequency of necrosis (54.8%, see Example 1).

Example 4

The Influence of Stagewise Co-Cultivation with Agrobacterium thumefaciens on the Frequency of Regeneration of Transgenic Shoots of Garden Strawberry of the Feyerverk Variety The frequency of the regeneration of transgenic shoots is one of the main characteristics of the efficiency of the method of genetic transformation. This efficiency is composed of the efficiencies of separate stages, starting with the preparation of explants and finishing with the composition of the medium for the selection and regeneration of transformants, and reflects the number of stable independent transformants on conversion to the initial number of the inoculated explants.

The total number of the transformants was calculated after four monthly passages on the RT medium and one passage on the M medium complemented with cefotaxirne and kanamycin. The data are presented in FIG. 6. From the diagram it is seen that from group A-1 to group A-4 the effectiveness of the transformation smoothly increases, and then on transition to A-5 it slightly decreases. The latter, most likely, is associated with lowering of the frequency of the transient GUS expression in this group, this, in its turn, lowering the frequency of formation of transgenic tissues. Another probable reason is lowering of the morpohogenetic potential in the case of long-term cultivation on hormone-free CC medium However, the characteristic in any case is higher than in control group B. The average figure for groups A-1-A5 is 1.72%, this being almost two times higher than the control variant. Therefore, the stagewise co-cultivation increases the frequency of the regeneration of transgenic shoots.

Example 5

The Influence of Stagewise Co-Cultivation with Agrobacterium thumefaciens on the Ratio of Direct Transformants and Transformants Produced Via Callus Stage It is known that the ratio of direct transformants and transformants produced via the callus stage depends mainly on the genotypic particulars of the plant (Masrcotrigiano et al. 1987; Suttter et al. 1997; Morozova, 2002). The developed method of genetic transformation of garden strawberry with the modified protocol of the preparation, inoculation and cultivation of explants is characterized by a higher proportion of direct transformants (Table 3).

TABLE 3

The influence of stagewise co-cultivation with *Agrobacterium thumefaciens* on the ratio of direct transformants and transformants produced via callus stage

| Protocol | Variety | Frequency of transformation, % | Proportion of direct transformants, % |
| --- | --- | --- | --- |
| According to the improved method of stagewise co-cultivation (A) | Feyerverk Selekta | 3.7 8.9 | 87.5 93.8 |
| According to the known method (James et al. (1990) and Nehra et al. (1990) (B) | Feyerverk Selekta | 1.0 1.8 | 28.3 42.0 |

Example 6

Data of the PCR Analysis of Transgenic Plants of Garden Strawberry of Feyerverk Variety, Produced with the Help of Binary Vector pBIThau35

Schestibratov et al. (2002), using an improved method of genetic transformation, produced transgenic plants of garden strawberry with the thaumatin genome. For studying T-DNA incorporation into the genome of kanamycin-resistant lines produced as a result of genetic transformations through the agency of the binary vector pBIThau35, a PCR analysis of samples of the total DNA was carried out. Since this vector provides transfer into the nucleus genome of two genes nptII and thauII, the introduction of T-DNA was analyzed separately for each sequence.

All the 23 independent transgenic lines are produced in stagewise selection on kanamycin in the concentration of 50 and 25 mg/l respectively in the first and subsequent passages. Then the produced regenerates were rooted on a medium with 25 mg/l of kanamycin. The PCR analysis of the samples of the total DNA for the presence of the fragment in 742 b.p. of the gene nptII has shown that all the lines contain genomic insert of the sequence under study. The results of the PCR analysis are presented in Table 4.

An analysis of the same samples of the total DNA with the use of a pair of primers to the sequence of the gene thauII has shown revealed that not all nptII-positive lines contain the insert of the gene of thaumatin II. PCR analysis has shown that the amplified fragment having the size of 878 b.p. was present in 18 out of 23 analyzed samples. The transgenic lines Clone 6, Clone 9, Clone 13, Clone 17 and Clone 20, in spite of the presence of the functioning insert of the gene nptII, did not contain the sequence of thaumatin II. The results of the PCR analysis are presented in Table 4.

Example 7

The Data of Western-Blot Analysis of Transgenic Plants of Garden Strawberry of the Feyerverk Variety, Produced with the Aid of Binary Vector pBITau35

The functionality of the introduced expression cassette 34S-thaumatin-3' nos was analyzed by Western-blotting. Protein immunodetection in the vegetative tissues (leaves) has shown that the expression cassette is functioning and protein is synthesized in 15 out of 18 thauII-positive independent lines. In the transgenic lines Clone 2, Clone 4 and Clone 12 thaumatin is not expressed. The reason accounting for this fact may be defective insertion of the cassette 35S-thaumatin-3' nos or endogenous suppression by homologous sequences. In the leaves of non-transgenic lines, as well as in the lines Clone 6, Clone 9, Clone 13, Clone 17 and Clone 20, without the insert 35S-thaumatin-3' nos the presence of thaumatin II is not detected. The collective results of the carried out Western-blot analysis in the leaves of the transgenic plants are presented in Table 4.

The immunological analysis of the thaumatin expression in the fruits of the transgenic plants has also confirmed the presence of protein (Table 4). The data correlate with the expression of thaumatin in the leaves.

TABLE 4

The results of PCR and Western-blot analyses of transgenic lines of garden strawberry (clones 1-23 and of the Feyerverk variety

| Type of plant | PCR analysis for nptII gene | PCR analysis for thauII gene | Immuno-detection of thaumatin in leaves | Immuno-detection of thaumatin in fruits |
| --- | --- | --- | --- | --- |
| Clone 1 | + | + | + | + |
| Clone 2 | + | + | − | − |
| Clone 3 | + | + | + | + |
| Clone 4 | + | + | − | − |
| Clone 5 | + | + | + | + |
| Clone 6 | + | − | − | − |
| Clone 7 | + | + | + | + |
| Clone 8 | + | + | + | + |
| Clone 9 | + | − | − | − |
| Clone 10 | + | + | + | + |
| Clone 11 | + | + | + | + |
| Clone 12 | + | + | − | − |
| Clone 13 | + | − | − | − |
| Clone 14 | + | + | + | + |
| Clone 15 | + | + | + | + |
| Clone 16 | + | + | + | + |
| Clone 17 | + | − | − | + |
| Clone 18 | + | + | + | + |
| Clone 19 | + | + | + | + |
| Clone 20 | + | − | − | − |
| Clone 21 | + | + | + | + |
| Clone 22 | + | + | + | + |
| Clone 23 | + | + | + | + |
| Feyerverk | − | − | − | − |

Example 8

The Data of Organoleptic Analysis of the Fruits of Garden Strawberry of Feyerverk Variety Tastings were carried out on the yields of garden strawberry for two years of cultivation on site for testing genetically improved plants on the territory of the VNIISPK (at Orel). The results of the tastings of the first year are presented in Table 5. The limited number of the first yield berries did not allow carrying out statistically reliable organoleptic analysis. Nevertheless, the average points evaluating the sweetness of the fruits; support a change in the taste properties of fruits of some transgenic lines. The sweetness of the fruit pulp was evaluated in terms of the five-point system, proceeding from the Feyerverk variety characteristic, according to which the taste of the mid-season fruits of the first yield is evaluated on an average by 4 points.

TABLE 5

Organoleptic analysis of sweetness of garden strawberry fruits of the first-year yield

| Tasting 1 | | Tasting 2 | | Tasting 3 | |
|---|---|---|---|---|---|
| Type of plant | Average score | Type of plant | Average score | Type of plant | Average score |
| Clone 3 | 4.1 | Clone 1 | 4.0 | Clone 3 | 4.0 |
| Clone 12 | 3.9 | Clone 17 | 3.8 | Clone 6 | 3.8 |
| Clone 11 | 4.0 | Clone 16 | 4.0 | Clone 7 | 4.0 |
| Clone 13 | 4.0 | Feyerverk | 3.9 | Clone 13 | 4.0 |
| Clone 22 | 4.2 | Clone 21 | 4.0 | Clone 8 | 3.9 |
| Feyerverk | 4.0 | Clone 12 | 3.9 | Clone 12 | 3.9 |

Pairwise comparison of the sweetness of berries with the thaumatin expression with control fruits has shown that in all the cases the scores of the experimental samples either excel the control ones (6 out of 9 pairs) or are equal to them (3 out of 9 pairs). Maximum exceedence of the sweetness of fruits with the thaumatin expression is 0.2 point. Such difference is registered in four pairs: Clone 3/Clone12; Clone 22/Feyerverk; Clone 1/Clone 17, Clone 3/Clone 6. In two cases the difference was 0.1 point: Clone 16/Feyerverk, Clone 21/Clone 12. Taking into account, in the first place, that for the Feyerverk variety the maximum score of the berries taste higher than 4 points is not typical, and, in the second place, the maximum score used in the selection practice is 4.5, the average taste score for Clone 22 exceeds appreciably the original variety characteristics.

The second-year yield proved to be more abundant and allowed carrying out statistically reliable organoleptic analysis of the fruits. The data are presented in Table 6.

Two tastings of the second-year yield have shown a reliable difference of five lines with the thaumatin expression out of the six selected ones from the control non-transgenic plants and lines without the thaumatin expression, except for the pair 3/13. The tasting scores for the second-year yield on an average are 0.2 point higher than those of the tasting of the first-year yield. This may be due to more favorable weather conditions contributing to the accumulation of sugars.

TABLE 6

Organoleptic analysis of sweetness of the second-year yield fruits of transgenic garden strawberry and of the Feyerverk variety

| Tasting 1 | | Tasting 2 | |
|---|---|---|---|
| Type of plant | Average score | Type of plant | Average score |
| Clone 3 | 4 ± 0.03 | Clone 16 | 4.2 ± 0.03 |
| Clone 12 | 4 ± 0.09 | Feyerverk | 4.1 ± 0.02 |
| Clone 1 | 4.5 ± 0.03 | Clone 22 | 4.4 ± 0.02 |
| Clone 13 | 4.1 ± 0.04 | Feyerverk | 4.2 ± 0.12 |
| Clone 8 | 4.3 ± 0.09 | Clone 21 | 4.3 ± 0.07 |
| Clone 6 | 4 ± 0.12 | Clone 6 | 4.1 ± 0.05 |

Example 9

The Influence of Thaumatin II Expression on the Resistance of Transgenic Lines of Garden Strawberry of the Feyerverk Variety to *Botrytis cinerea*

Basing on the results of CPR analysis and Western blotting, from the transgenic lines of strawberry produced by an improved method (Schestibratov et al. 2002) three clones were selected with the thaumatin expression level of at least 0.2 μg per mg of total protein, namely, Clone3, Clone 7 and Clone 8, and also one clone without the expression (Clone 17). Leaves from wild-type plants, from the lines without thaumatin expression (Clone 17) and from the transgenic line Clone GUS, produced with the use of the vector construct pBI121 were used as negative control.

Preliminary experiments have shown that the results of analyses are strongly influenced not only by the age of the plant tissue and the condition of the *Botrytis cinerea* inoculum, but also by the conditions under which the infected leaf disks are incubated. In the present case the key factor is the humidity of the chamber and of the filter supports. This factor affected not so much the character of the infection as the rate of colonization of leaf disks. Visual evaluation of the pathogen development was carried out after definite time intervals, for this reason humidity produced decisive influence on the results of comparison. Visual evaluation of necrosis, carried out on the sixth day after the inoculation, has given the following results: the mean area of affection was 27.5±12.9% for the Clone GUS, while on the disks of Clone 7 necrotic zones are not formed yet. The data about this and other pairs are presented in Table 7.

The data about the extent of sporogenesis, presented in Table 10 were registered on the ninth day after the inoculation (in contradistinction to the data about necrosis), since conidiofores are formed on mycelium with a delay of several days after the appearance of necrotic zones on leaf disks. Average scores of necrosis for example, for the Clone 7/Clone GUS pair were 0.13±0.06/0.47±0.21 for the experimental and control variants, respectively.

Therefore, the data about the necrosis of leaf disks confirm statistically reliable differences not only within the pairs being compared but also between all the transgenic lines with the thaumatin expression on the one hand and the control plants on the other hand. The second criterion used by us for evaluating the resistance of plants to the infection caused by *Botrytis cinerea* also supports reliable differences within the pairs being compared, with the sporogenesis on the leaf disks of plants with the thaumatin expression having been substantially inhibited.

TABLE 7

The results of test for the resistance of leaf disks of transgenic garden strawberry and of the Feyerverk variety to *Botrytis cinerea*

| Clone | Thaumatin accumulation level, μg/kg of total protein | Mean area of necrosis, % | Mean score of sporogenesis | Resistance enhancement index |
|---|---|---|---|---|
| Clone 7 | 1.5 | 0 | 0.13 ± 0.06 | 3.6 |
| Clone GUS | 0 | 27.5 ± 12.9 | 0.47 ± 0.21 | — |
| Clone 8 | 1 | 0.7 ± 0.3 | 0.07 ± 0.06 | 3.0 |
| Feyerverk | 0 | 5.7 ± 5.5 | 0.21 ± 0.11 | — |
| Clone 3 | 0.2 | 1 ± 0.8 | 0.13 ± 0.06 | 2.8 |
| Clone 17 | 0 | 19.7 ± 6.1 | 0.37 ± 0.11 | — |

Example 10

Field Testing Data of Transgenic Plants

Field testing of transgenic plants was carried out on the certified site for field testing of transgenic plants, created on the basis of the VNIISPK quarantine garden (at Orel). The vegetative and generative activities of field plants were evaluated according to four main criteria: the number of rosettes in a shrub; the average height of the shrub; the average number of peduncles; and the weight of ripe first-yield berries. After two years of growth in open ground conditions, the major part of transgenic lines did not display undesirable phenotypic variations (Table 8). However, several lines (Clone 9, Clone 14, Clone 15, Clone 128, Clone 19, Clone20, Clone 23) differed in the main characteristics from control non-transgenic plants and from the majority of other transgenic strawberry plants. Lines with somaclonal variations were visually detected mainly by the height of the shrub and by the yield (by the weight of the ripe first-yield berries). Eventually, an analysis for correspondence with the prototype has shown that 16 transgenic lines out of 23 in terms of the main characteristics of the vegetative and generative activities correspond to the Feyerverk variety. Therefore, the optimized method of genetic transformation of garden strawberry, described in the present invention, is characterized by an approximately 70% effectiveness of producing plants without somaclonal variations.

TABLE 8

The results of field testing of transgenic plants of garden strawberry and of the Feyerverk variety: evaluation of the vegetative and generative activities

| Type of plant | Number of rosettes in a shrub | Average height of shrub, cm | Average number of peduncles | Weight of first-yield berries, g | Somaclonal variation |
|---|---|---|---|---|---|
| Clone 1 | 2.3 ± 0.3 | 23.5 ± 4.9 | 7.1 ± 3.1 | 255 ± 52 | − |
| Clone 2 | 3.7 ± 1.3 | 22.5 ± 1.7 | 5.8 ± 2 | 102 ± 15 | − |
| Clone 3 | 3.2 ± 0.8 | 24.7 ± 5.4 | 5 ± 2.6 | 120 ± 22 | − |
| Clone 4 | 3.5 ± 0.9 | 25.5 ± 2.8 | 5 ± 0.7 | 210 ± 44 | − |
| Clone 5 | 3.4 ± 0.7 | 27 ± 8.9 | 5.9 ± 2.3 | 285 ± 35 | − |
| Clone 6 | 3.9 ± 1.6 | 22.2 ± 0.9 | 5.3 ± 1.5 | 289 ± 56 | − |
| Clone 7 | 3.5 ± 1 | 26.2 ± 2.8 | 6.5 ± 1.8 | 209 ± 36 | − |
| Clone 8 | 3.8 ± 1.1 | 28.5 ± 12 | 5.8 ± 0.4 | 159 ± 41\ | − |
| Clone 9 | 3.3 ± 1.3 | 19.8 ± 1.9 | 2.3 ± 1.7 | 43 ± 13 | + |
| Clone 10 | 3.5 ± 0.8 | 21.5 ± .5 | 4.9 ± 0.5 | 250 ± 23 | − |
| Cone 11 | 3.3 ± 0.3 | 21 ± 3 | 4.4 ± 0.7 | 198 ± 17 | − |
| Clone 12 | 3.5 ± 0.7 | 24.5 ± 1.1 | 4.9 ± 2.4 | 167 ± 18 | − |
| Clone 13 | 3.2 ± 1.6 | 22.3 ± 2.3 | 3.3 ± 1.3 | 198 ± 23 | − |
| Clone 14 | 2.3 ± 0.9 | 6.9 ± 3.1 | 1.7 ± 1.2 | 0 | + |
| Clone 15 | 2.5 ± 0.7 | 14.3 ± 1.2 | 1.8 ± 0.3 | 0 | + |
| Clone 16 | 3.2 ± 1 | 22.9 ± 4.2 | 3.2 ± 1.1 | 302 ± 98 | − |
| Clone 17 | 3.7 ± 0.3 | 25.1 ± 1.9 | 4.1 ± 1 | 277 ± 63 | − |
| Clone 18 | 2.4 ± 1 | 10.1 ± 2.5 | 2..7 ± 1.5 | 78 ± 14 | + |
| Clone 19 | 2.2 ± 0.3 | 15.3 ± 1.1 | 2.1 ± 0.4 | 35 ± 15 | + |
| Clone 20 | 3.6 ± 0.9 | 12.7 ± 0.9 | 1.2 ± 1.2 | 0 | + |
| Clone 21 | 3.5 ± 0.5 | 24.8 ± 1.3 | 6.1 ± 1.4 | 319 ± 78 | − |
| Clone 22 | 3.7 ± 1.5 | 24.5 ± 2 | 4.4 ± 2.1 | 288 ± 58 | − |
| Clone 23 | 2.2 ± 0.8 | 11.3 ± 2.5 | 1.5 ± 0.5 | 83 ± 26 | + |
| Feyerverk | 3.2 ± 0.7 | 24.2 ± 2.9 | 4.8 ± 1 | 266 ± 35 | − |

Example 11

Figure 7:
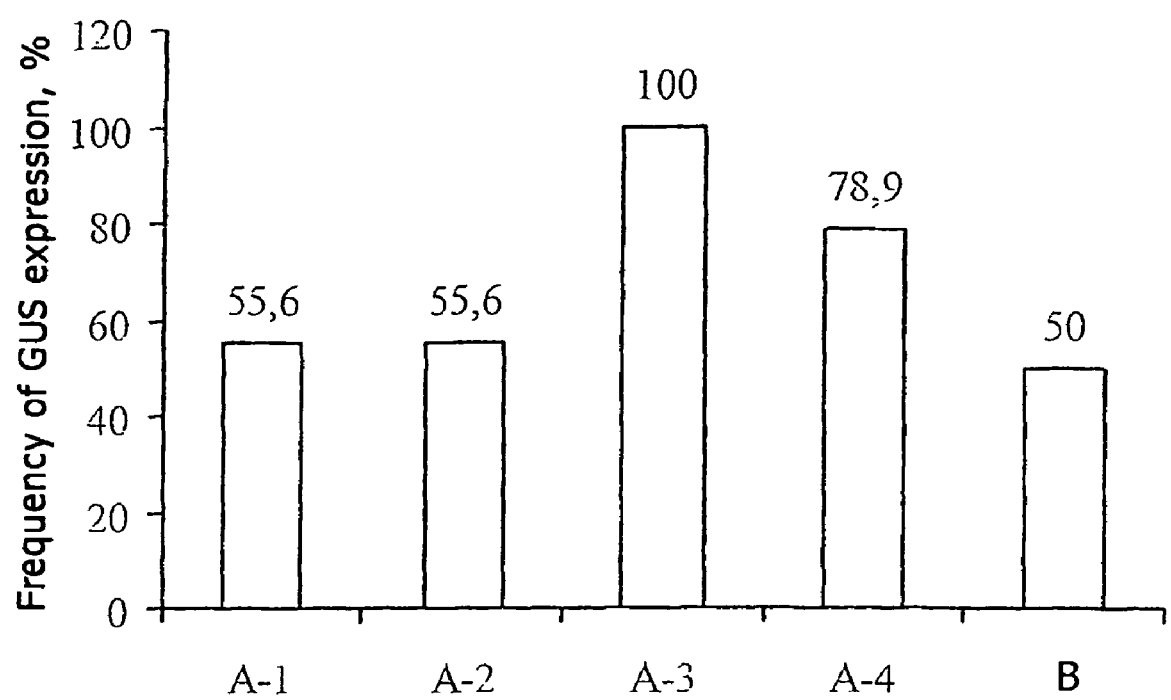
FIG. 7 illustrates the influence of stagewise co-cultivation with *Agrobacterium thumefaciens* on the transgenic GUS-expression in the tissues of explants of apple.

The Influence of Stagewise Co-Cultivation with *Agrobacterium thumefaciens* on Transient GUS Expression in Tissues of Apple Explants In the genetic transformation of apple of the Melba variety with the use of the improved protocol in the stage of transient GUS expression a higher frequency thereof was observed in groups A-3 and A-4 of variant A (as against control variant B). The results of the analysis are presented in FIG. 7. Similarly to the case with the garden strawberry, the frequency of the GUS expression was evaluated on conversion to the number of sections which have gone interaction with agrobacteria, rather than on the number of explants. Apart from an increase of the GUS expression frequency, a change in the intensity of the GUS activity was observed. In variant A concurrently with the growth of the frequency, there took place an increase of the GUS staining intensity of explants after incubation in X-Gluc solution.

Example 12

Data of CPR and Western-Blotting Analyses of Transgenic Plants of Apple Produced with the Aid of Binary Vector pBIThau35

By the improved method of genetic transformation there were produced 2 independent transgenic lines of apple. The obtained regenerates were rooted on a medium with 25 mg/l of kanamycin. The PCR analysis of samples of the total DNA for the presence of a fragment having 742 b.p. of the gene nptII and of a fragment of the gene thauII having a size of 878 b.p. has shown that all the lines contain genomic inserts of two sequences (Table 9). The immunodetection of protein in the vegetative tissues (leaves) of plants in vitro and in vivo has shown that the expression cassette is functioning and protein is formed in both lines (Table 9).

TABLE 9

Results of PCR and Western-blotting analyses of transgenic lines of apple of Melba variety

| Type of plant | PCR analysis for nptII gene | PCR analysis for thauII gene | Immuno-detection of thaumatin in leaves in vitro | Immuno-detection of thaumatin in leaves in vivo |
|---|---|---|---|---|
| Clone M-I-1 | + | + | + | + |
| Clone M-I-2 | + | + | + | + |
| Melba | − | − | − | − |

Example 13

Data of CPR Analysis of Transgenic Plants of Selekta Variety, Produced with the Aid of Binary Vector pBIThau35

Using the improved method of genetic transformation, there were produced 15 independent transgenic lines. The obtained regenerants were rooted on a medium with 25 mg/l of kanamycin. The PCR analysis of samples of the total DNA for the presence of a fragment having 742 b.p. of the gene nptII has shown that all the lines contain a genomic insert of the sequence being studied. The results of the PCR analysis are presented in Table 10.

An analysis of the same samples of the total DNA with the use of a pair of primers to the sequence of the gene thauII has revealed, that not all nptII-positive lines contain the insert of the gene of thaumatin II. The PCR analysis has shown that the fragment being amplified, having a size of 878 b.p., was present in 13 out of 15 samples being analyzed. Transgenic lines Clone S4, Clone S9, in spite of the presence of the functioning insert of the gene nptII, did not contain the sequence of thaumatin II. The results of the PCR analysis are presented in Table 10.

Example 14

Data of Western-Blot Analysis of Transgenic Plants of Selekta Variety Produced with the Aid of Binary Vector pBIThau35

The immunodetection of protein in the vegetative tissues (leaves) has shown that the expression cassette is functioning and protein is synthesized in all (13) of the thauII positive independent lines. In the leaves of non-transgenic lines, like in the lines Clone S4, Clone S9 without the insert 35S-thaumatin-3'nos, the presence of thaumatin II is not detected. The results of the carried out Western-blotting analysis are presented in Table 10.

TABLE 10

Results of PCR and Western-blotting analyses of transgenic lines of garden strawberry (clones S1-S15) and of Selekta variety

| Type of plant | PCR analysis for gene nptII | PCR analysis for gene thauII | Immuno-detection of thaumatin in leaves | Immuno-detection of thaumatin in fruits |
|---|---|---|---|---|
| Clone S1  | + | + | + | + |
| Clone S2  | + | + | + | + |
| Clone S3  | + | + | + | + |
| Clone S4  | + | − | − | − |
| Clone S5  | + | + | + | + |
| Clone S6  | + | + | + | + |
| Clone S7  | + | + | + | + |
| Clone S8  | + | + | + | + |
| Clone S9  | + | − | − | − |
| Clone S10 | + | + | + | + |
| Clone S11 | + | + | + | + |
| Clone S12 | + | + | + | + |
| Clone S12 | + | + | + | + |
| Clone S13 | + | + | + | + |
| Clone S14 | + | + | + | + |
| Clone S15 | + | + | + | + |
| Selekta   | − | − | − | − |

The immunological analysis of the thaumatin expression in the fruits of transgenic lines has also confirmed the presence of protein. The data correlate with the thaumatin expression in leaves.

TABLE 11

Results of field testing of transgenic plants of garden strawberry (lines S1-S15) and of Selekta variety: evaluation of vegetative and generative activities

| Type of plant | Average height of shrub, cm | Average number of peduncles | Average weight of a berry, g | Somaclonal variations |
|---|---|---|---|---|
| Clone S1  | 21.5 ± 2.3 | 3.3 ± 1.2 |  | − |
| Clone S2  | 18 ± 1.9   | 3 ± 1.3   |  | − |
| Clone S3  | 21 ± 4     | 2.7 ± 1.6 |  | − |
| Clone S4  | 23.5 ± 2.8 | 2.3 ± 1.2 |  | − |
| Clone S5  | 21 ± 4.9   | 2 ± 0.6   |  | − |
| Clone S6  | 20.6 ± 1.9 | 1.5 ± 1   |  | − |
| Clone S7  | 22.2 ± 2.8 | 2.3 ± 0.8 |  | − |
| Clone S8  | 18.5 ± 2   | 2.8 ± 0.8 |  | − |
| Clone S9  | 14.8 ± 1   | 3.2 ± 2   |  | + |
| Clone S10 | 11.5 ± 2.5 | 0.7 ± 0.5 |  | + |
| Clone S11 | 20 ± 3     | 0.3 ± 0.1 |  | + |
| Clone S12 | 21.5 ± 2.1 | 1.5 ± 0.8 |  | − |
| Clone S13 | 12.3 ± 1.3 | 3.7 ± 2   |  | + |
| Clone S14 | 10.7 ± 3   | 2.2 ± 1   |  | + |
| Clone S15 | 19.4 ± 4.2 | 1.7 ± 1   |  | − |
| Selekta   | 20.2 ± 1.8 | 2 ± 0.8   |  | − |

Example 15

Field Testing Data of Transgenic Plants of Selekta Variety

The vegetative and generative activities of field plants were evaluated according to the following main criteria: the average height of the shrub; the average number of peduncles; and the average weight of the berry. The analysis for the correspondence to the variety type has shown that 10 out of 15 transgenic lines in terms of the main characteristics of the vegetative and generative activities correspond to the Selekta variety. The lines with somaclonal variations were detected visually mainly by the height of the shrub, the number of peduncles, and the average weight of the berries (Table 11). Thus, the optimized method of the genetic transformation of garden strawberry, described in the present invention, is characterized by the effectiveness of producing plants without somaclonal variations equal to 66.7%, this being in good correlation with the data on the Feyerverk variety.

Example 16

Data of Organoleptic Analysis of Fruits of Transgenic Lines of Garden Strawberry of Selekta Variety Pairwise comparison of the sweetness of the berries with the thaumatin expression with the control fruits has demonstrated that the characteristics of the experimental samples either excel or are equal to the control ones. Tasting has shown reliable enhancement of the sweetness in two lines (Clones S2 and S3) out of five with the thaumatin expression, selected for the analysis (Table 12). Maximum exceedence of the sweetness of fruits with the thaumatin expression is 0.3 point.

TABLE 12

Organoleptic analysis of sweetness of fruits of transgenic lines of garden strawberry and of Selekta variety

| Tasting 1 | | Tasting 2 | |
|---|---|---|---|
| Type of plant | Average score | Type of plant | Average score |
| Clone S1 | 4 ± 0.03  | Clone S4  | 4 ± 0.07 |
| Clone S2 | 4.3 ± 0.05 | Clone S6  | 4 ± 0.13 |
| Clone S3 | 4.2 ± 0.05 | Clone S10 | 4 ± 0.08 |
| Selekta  | 4 ± 0.07  | Selekta   | 4 ± 0.14 |

INDUSTRIAL APPLICABILITY

The improved method of the preparation, inoculation and co-cultivation of explants has excelled all the effectiveness characteristics of the method of genetic transformation. The present method is characterized by a low frequency of the necrosis of explants, an enhanced frequency of transient expression, an enhanced frequency of the transformation of transgenic tissues, an enhanced frequency of the regeneration of transgenic shoots, a higher proportion of direct transformants, a low frequency of somaclonal variations.

The method of genetic transformation, described in the present invention, has made it possible to produce a sufficient number of transgenic lines of garden strawberry of the Feyerverk and Selekta varieties, and draw confirmation of the effectiveness of the method in the genetic transformation of apple of the Melba variety. In the process of laboratory and field testing of the Feyerverk and Selekta varieties, success was made in selecting a number of lines with pronounced improved agronomic characteristics (improved taste of berries, enhanced resistance to grey mildew). Moreover these lines did not feature undesirable phenotypic variations which often originate in the in vitro regeneration of garden strawberry via the callus stage.

The improved method of the transformation provides an ample opportunity fort selecting genetic material for producing phytopathogen-resistant plants, plants oriented to the synthesis of proteins useful in pharmacology.

REFERENCES

Rovenkova E. V. et al. (1994). Development of a new vector system based on *Agrobacterium thumefaciens* A281 strain. Abstracts of Annual Conference "Genetic and Cell Engineering". State Scientific and Technical Program of Russia "New Methods of Bioengineering", [Moscow, 1994].

Abad L. R et al. (1996) Antifungal activity of tobacco osmotin has specificity and involves plasma membrane permeabilization. Plant Science 118: 11-23.

Boxus P. H. (1974) The production of strawberry plants by in vitro propagation. J. Hort. Sci. 49: 209-210.

De Mesa M. C. et al. (2000) *Agrobacterium* cells as microprojectile coating stable transformation rates in strawberry. Aust J. Plant Physiol. 27: 1093-1100.

Dier et al. (2001) Methods for strawberry transformation using *Agrobacterium thumefaciens*. U.S. Pat. No. 6,274,791.

Dolgov S. V. et al. (1999). Expression of thaumatin II gene in horticultural crops. In: Developments in plant breeding. Vol. 8 "Genetics and Breeding for Crop Quality and Resistance" ed. S. Mugnozza, E. Porceddu and M. Pagnotta. Kluwer Ac. Publ. Dordrecht, Boston, London, pp 165-172.

du Plessis H. J. et al. (1997). Efficient genetic transformation of strawberry (*Fragaria* x *ananassa* duch.) Cultivar Selekta. ActaHort. (ISHS) 447:289-294.

Edens L. et al. (1982) Cloning of cDNA encoding the sweet-tasting plant protein thaumatin and its expression mE. coll. Gene. 18(1): 1-12.

Humara J. M. et al. (1999) *Agrobacterium tumefaciens*-mediated transformation of *Pinus pinea* L. cotyledons: an assessment of factors influencing the efficiency of uidA gene transfer Plant Cell Reports 19:51-58

James D. J. et al. (1990) *Agrobacterium*-mediated transformation of the cultivated strawberry (*Fragaria ananassa* Duch.) using disarmed binary vectors. Plant Sci 69: 79-94.

Jefferson R. A. (1987) Assaying chimeric genes in plants: the GUS gene fusion system. Plant Molecular Biology Reporter 5: 387-405.

Linthorst H. J. M. et al. (1989) Constitutive expression of pathogenesis-related proteins PR-1, GPR and PR-S in tobacco has no effect on virus infection. Plant Cell 1:285-291.

Maniatis T. et al. (1982) Molecular Cloning: A laboratory manual, Cold Spring Harbor Press, N.Y.

Marcotrigiano M. et al. (1987) Histogenic instability in tissue culture proliferated strawberry plants. J. Amer. Soc. Hort. Sci. 112: 583-587.

Mathews H. et al. Plant genetic transformation methods and transgenic plants. U.S. Pat. No. 5,750,870. (May 12, 1998).

Morozova T. (2002). Genetic stability of pure lines of *Fragaria vesca*. in micro-propagation and long-term storage in vitro. Acta Hort. (ISHS) 567:85-88

Mussinan C. J. et al. (1975) Organic acid from fresh California strawberries. J Agric. Food Chem. 23: 482-82.

Murashige T. et al. (1962) A revised medium for rapid growth and bioassay with tobacco tissue culture. Physiol. Plant., 15: 473-97.

Nehra N. S. et al. (1990b) Genetic transformation of strawberry by *Agrobacterium thumefaciens* using a leaf disk regeneration system. Plant Cell Rep. 9: 293-298.

Olhoft P. M. et al. (2001) The role of thiol compounds in increasing *Agrobacterium*-mediated transformation of soybean cotyledonary-node cells. Plant Cell Rep. 20:731-737

Peng G. et al. (1991) Evaluation of microorganisms for biocontrol of *Botrytis cinerea* in strawberry. Canadian Journal of Plant Pathology 13: 247-257.

Perl A et al. (1996) Establishment of an *Agrobacterium*-mediated transformation system for grape (*Vitis vinifera* L.): the role of antioxidants during grape-*Agrobacterium* interactions. Nat. Biotechnol. May; 14(5):624-8.

Roberts W. K. et al. (1990) Zeamatin, an antifungal protein from maize with membrane-permebealizing activity. J. Gen. Microbiol. 136: 1771-1778.

Linthorst H. J. M. (1991) Pathogenesis-related proteins of plants. Crit. Rev. Plant Sci. 10:123-150.

Rogers S. et al. (1995) Extraction of total cellular DNA from plants, algae and fungi.//Gelvin S., Schiperoort R. (Eds.) Plant Molecular Biology Manual. Kluwer Academic Publishers Dordrecht, Boston, London. Section 7-1

Schestibratov K et al. (2001) Plant regeneration from excised cotyledons of *pinus radiata*./in Abstracts of 43rd ETCS Congress, Granada, Spain, Sep. 30-Oct. 3, 2001.

Schestibratov K. A. et al. (2002) Molecular breeding of strawberry cv. Firework for enhanced disease resistance and taste improvement by introduction of thauII and rs-afp3 genes./in Abstracts of the Agricultural Biotechnology International Conference, Saskatoon, Canada, Sep. 15-18, 2002.

Stintzi A et al. (1993) Plant "pathogenesis-related" proteins and their role in defense against pathogens. Biochemie 75: 687-706.

Sutler, E. et al. (1997) Direct regeneration of strawberry (*Fragaria* x *ananassa* duch.) from leaf disks. Acta Hort. (ISHS) 447:243-246.

Szwacka M et al. (2002) Variable properties of transgenic cucumber plants containing the thaumatin II gene from *Thaumatococcus daniellii*. Acta Physiologiae Plantarum, 24 (2) pp. 173-185, 2002.

Trinh H. et al. (2001) Regeneration and transformation methods./EMBO Practical Course on the New Plant Model System Medicago truncatula Gif-sur-Yvette France (Nov. 19-Dec. 1 st 2001).

Sambrook J. et al. (1989) Molecular cloning: A Laboratory Manual, 2nd Edition, Cold Spring Harbor Laboratory, Cold Spring Harbor, N.Y.

Hansen G. Plant transformation methods U.S. Pat. No. 6,162,965 (Dec. 19, 2000).

Baker, B. J. et al. Non-pathogen induced systemic acquired resistance (SAR) in plants. U.S. Patent Appl. 20020004944 (Jan. 10, 2002)

Ryals J. A. et al. Method of protecting plants from oomycete pathogens. U.S. Pat. No. 5,856,154 (Jan. 5, 1999).

Stuart D. A. et al. Enhanced somatic embryogenesis using maltose. U.S. Pat. No. 4,801,545 (Jan. 31, 1989).

Verrips C. T. et al. DNA sequences encoding the various allelic forms of mature thaumatin, and cloning vehicles, etc. U.S. Pat. No. 4,891,316 (Jan. 2, 1990).

The invention claimed is:

1. A method of producing a transgenic strawberry plant comprising inoculation of tissue of a strawberry plant, with *Agrobacterium thumefaciens* which comprises at least one vector comprising at least one gene of interest wherein in the step of transformation a stage wise co-cultivation of explants is used which comprises the steps of:
   a) cutting leaves into individual leaf disks for preparing explants;
   b) cutting one or more narrow strips having a width not exceeding 2 mm from the leaf disks for the inoculation of the leaf disks;
   c) inoculating and co-cultivating the leaf disk obtained in step b) with the bacterial suspension and subsequently removing excess bacteria and incubating the leaf disk at 25-28° C. in darkness;
   d) forming first-stage explants having a width from 1 to 3 mm from the side of the first section of leaf disks by step b) incubating in darkness first-stage explants in a 23-25° C. and the leaf disks in a 25-28° C.
   e) forming from 2 to 5 next-stages explants having a width from 1 to 3 mm with a periodicity of 1 to 5 days by independent steps, selecting prepared explants that have a lowered frequency of necrotic reactions and
   f) allowing the selected explants to develop into a transgenic strawberry plant.

2. The method according to claim 1, wherein the vector contains genetic material that codes for at least one target protein.

3. The method according to claim 1, wherein the vector contains genetic material that codes for at least one protein which contributes to lowering necrosis in the step of transformation.

4. The method according to claim 1, wherein the vector contains genetic material that codes for at least one protein which enhances plant resistance to phytopathogens and which is selected from the group consisting of PR-1, PR-2, PR-3, PR-4, and PR-5.

5. The method according to claim 1, wherein the vector contains genetic material that codes for a combination of proteins according to claim 2, 3 or 4.

6. The method according to claim 4 wherein the vector contains genetic material that codes for thaumatin, belonging to PR-5.

7. The method according to claim 4, wherein genetic material codes for a protein that enhances resistance to fungi selected from the group consisting of *Phytophthora fragariae, Verticillium alboatrum, Mycospaerella fragariae, Diplocarpon earliana, Dendxrophoma obscurans, Botrytis cinerea,* and *Sphaerotheca humuli.*

8. The method according to claim 1, wherein the strawberry plant is selected from the group of varieties: Selekta, Chambly, Chandler, Oka, Yamaska, L'Acadie, L'Authentique Orleans, Rosalyne, Roseberry, Saint-Pierre, Donna, Enzed Levin, Enzed Lincoln, Vilanova, Durval, Redcrest, Bountiful, Redgem, Pelican, Primtime, Mohawk, Latestar, Winoma, and Feyerverk.

9. A method for producing a transgenic strawberry, comprising treating a tissue of a strawberry plant with *Agrobacterium tumefaciens* which comprises at least one vector comprising at least one gene of interest wherein the method comprises the steps of:
   a) cutting leaves into individual leaf disks for preparing explants;
   b) cutting one or more narrow strips having a width not exceeding 2 mm from the leaf disks for the inoculation of the leaf disks;
   c) inoculating and co-cultivating the leaf disk obtained in step b) with the bacterial suspension and subsequently removing excess bacteria;
   d) forming first-stage explants having a width from 1 to 3 mm from the side of the first section of leaf disks by step b);
   e) forming from 2 to 5 next-stage explants having a width from 1 to 3 mm with a periodicity of 1 to 5 days by independent steps;
   f) transferring the explants onto selection and regeneration medium comprising from 1 to 10 mg/ml TDZ, from 0 to 2 mg/l IBA and from 10 to 100 mg/l kanamycin
   g) selecting prepared explants that have a lowered frequency of necrotic reactions; and
   h) allowing the selected explants to develop into a transgenic strawberry plant.

10. The method according to claim 9, wherein the concentration of TDZ is 5 mg/l.

11. The method according to claim 9 wherein the concentration of IBA is 0.3 mg/l.

12. The method according to claim 9, wherein the concentration of kanamycin is 50 mg/l.

13. The method according to claim 9, wherein the ratio of the section length and the explant surface area is from 0.1 mm/mm$^2$ to 2 mm/mm$^2$.

14. The method according to claim 9, wherein the ratio of the section length and the explant surface area is 0.5 mm/mm$^2$.

15. A method of producing a transgenic strawberry, comprising treating the tissue of a strawberry plant with *Agrobacterium tumefaciens* which comprises at least one vector comprising at least one gene of interest, wherein the method comprises the steps of:
   (i) selecting at least one leaf disk from said strawberry plant;
   (ii) separating a segment from the disk to allow bacteria access;
   (iii) inoculating the leaf disk with agrobacteria and subsequently removing excess agrobacteria;
   (iv) excising explant from the inoculated disk and wherein the remainder of the inoculated disk is inoculated for 1 to 5 days to allow subsequent inoculation with agrobacteria before excising 2 to 5 further explants;
   (v) transferring the explant excised in step (iv) onto selection and regeneration media comprising from 1 to 10 mg TDZ, from 0-0.3 mg IBA, and from 10 to 100 mg kanamycin;
   (vi) selecting prepared explants that have a lowered frequency of necrotic reactions; and
   (vii) allowing the selected explants to develop into a transgenic strawberry plant.

* * * * *